(12) United States Patent
Chan et al.

(10) Patent No.: US 11,109,168 B2
(45) Date of Patent: Aug. 31, 2021

(54) EXTERNAL DEVICE OF PROSTHESIS CONNECTOR

(71) Applicants: Eddie Sze Chuen Chan, Macquarie University (AU); Tadeusz Jurkiewicz, Macquarie University (AU)

(72) Inventors: Eddie Sze Chuen Chan, Macquarie University (AU); Tadeusz Jurkiewicz, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 540 days.

(21) Appl. No.: 15/599,668

(22) Filed: May 19, 2017

(65) Prior Publication Data
US 2018/0338209 A1    Nov. 22, 2018

(51) Int. Cl.
| H04R 25/00 | (2006.01) |
| A61N 1/36 | (2006.01) |
| A61N 1/372 | (2006.01) |
| A61N 1/378 | (2006.01) |

(52) U.S. Cl.
CPC ....... *H04R 25/556* (2013.01); *A61N 1/36036* (2017.08); *A61N 1/3787* (2013.01); *A61N 1/37211* (2013.01); *H04R 25/60* (2013.01); *H04R 25/602* (2013.01); *H04R 25/607* (2019.05); *H04R 2225/0213* (2019.05); *H04R 2225/31* (2013.01)

(58) Field of Classification Search
CPC ................ H04R 25/556; H04R 25/602; H04R 2205/021; H01M 2/1022; H01M 2/1094; H01R 13/35; H01R 13/64; H01R 24/38
See application file for complete search history.

(56) References Cited

U.S. PATENT DOCUMENTS

| 4,469,765 | A | * | 9/1984 | McCartney | ......... | H01M 2/0202 |
| | | | | | | 429/123 |
| 4,637,674 | A | * | 1/1987 | Kobler | ............... | H01R 13/5219 |
| | | | | | | 439/271 |
| 4,709,974 | A | * | 12/1987 | Hawkins | ................. | H01M 2/20 |
| | | | | | | 439/341 |
| 6,482,036 | B1 | * | 11/2002 | Broussard | ............ | H01R 13/523 |
| | | | | | | 439/606 |
| 6,538,413 | B1 | * | 3/2003 | Beard | ................. | G06F 12/1408 |
| | | | | | | 307/116 |

(Continued)

FOREIGN PATENT DOCUMENTS

DE    3723809 A1 *  1/1989    ........... H04R 25/556

OTHER PUBLICATIONS

Martin Cosenza, "Believed Prior Art Document 1", believed to be known or used by others before May 2017.

(Continued)

*Primary Examiner* — Ryan Robinson
(74) *Attorney, Agent, or Firm* — Pilloff Passino & Cosenza LLP; Martin J. Cosenza

(57) ABSTRACT

An external device of a prosthesis, including an electronics component, which can be a sound processor of a hearing prosthesis, and a power component, which can be a battery, the power component being removably attached to the electronics component, wherein the BTE device is configured with electrostatic discharge protection between the electronics component and the power component.

25 Claims, 39 Drawing Sheets

(56) References Cited

U.S. PATENT DOCUMENTS

| | | | | |
|---|---|---|---|---|
| 6,546,110 B1* | 4/2003 | Vonlanthen | H04R 25/556 | |
| | | | 381/314 | |
| 7,097,746 B1* | 8/2006 | Tziviskos | H01R 9/0518 | |
| | | | 204/196.23 | |
| 7,142,926 B2* | 11/2006 | Crawford | H04R 25/606 | |
| | | | 607/55 | |
| 7,558,894 B1* | 7/2009 | Lydon | G06F 1/266 | |
| | | | 710/105 | |
| 7,660,633 B2* | 2/2010 | Darley | H04R 1/1091 | |
| | | | 607/57 | |
| 8,043,123 B2* | 10/2011 | Hsieh | H01R 13/04 | |
| | | | 439/637 | |
| 8,103,032 B2* | 1/2012 | Ho | H04R 25/602 | |
| | | | 381/322 | |
| 8,437,860 B1* | 5/2013 | Crawford | H04R 25/60 | |
| | | | 607/1 | |
| 8,591,239 B2* | 11/2013 | Dai | H04R 25/556 | |
| | | | 439/133 | |
| 8,660,658 B2* | 2/2014 | Walsh | H04R 25/02 | |
| | | | 607/57 | |
| 9,071,896 B2* | 6/2015 | Goodman | H01M 2/1038 | |
| 9,071,917 B2* | 6/2015 | Neumeyer | H04R 25/556 | |
| 9,100,764 B2* | 8/2015 | Solum | H04R 25/602 | |
| 9,459,326 B2* | 10/2016 | McGrath | G01R 31/3648 | |
| 9,788,130 B2* | 10/2017 | Muller | H04R 1/1041 | |
| 9,832,577 B2* | 11/2017 | Karunasiri | A61N 1/36036 | |
| 9,930,459 B2* | 3/2018 | Cano | H04R 25/602 | |
| 10,179,240 B2* | 1/2019 | Busby | A61B 5/125 | |
| 10,264,373 B2* | 4/2019 | Karlsen | H04R 25/65 | |
| 2004/0196599 A1* | 10/2004 | Kim | H01R 13/2442 | |
| | | | 361/18 | |
| 2007/0197085 A1* | 8/2007 | Li | H01R 13/2442 | |
| | | | 439/500 | |
| 2015/0110322 A1* | 4/2015 | Andersson | H04R 25/552 | |
| | | | 381/326 | |
| 2016/0165367 A1* | 6/2016 | Ochsenbein | H04R 25/602 | |
| | | | 381/323 | |
| 2016/0381472 A1* | 12/2016 | Feeley | H04R 25/604 | |
| | | | 381/322 | |
| 2017/0064469 A1* | 3/2017 | Spidsbjerg | H04R 25/556 | |
| 2017/0311099 A1* | 10/2017 | Vardfjall | H04R 25/602 | |
| 2018/0343525 A1* | 11/2018 | Karlsen | H04R 25/02 | |

OTHER PUBLICATIONS

Martin Cosenza, "Believed Prior Art Document 2", believed to be known or used by others before May 2017.

Martin Cosenza, "Believed Prior Art Document 3", believed to be known or used by others before May 2017.

\* cited by examiner

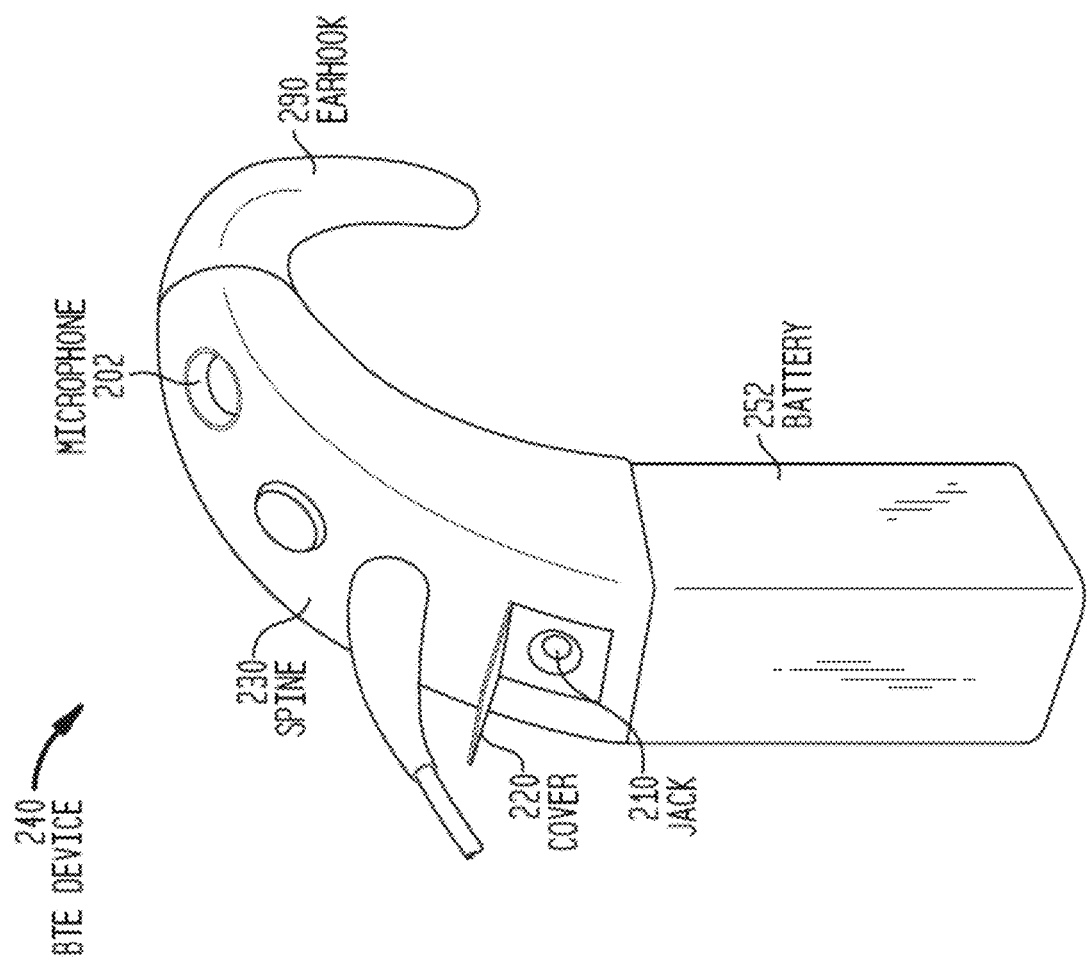

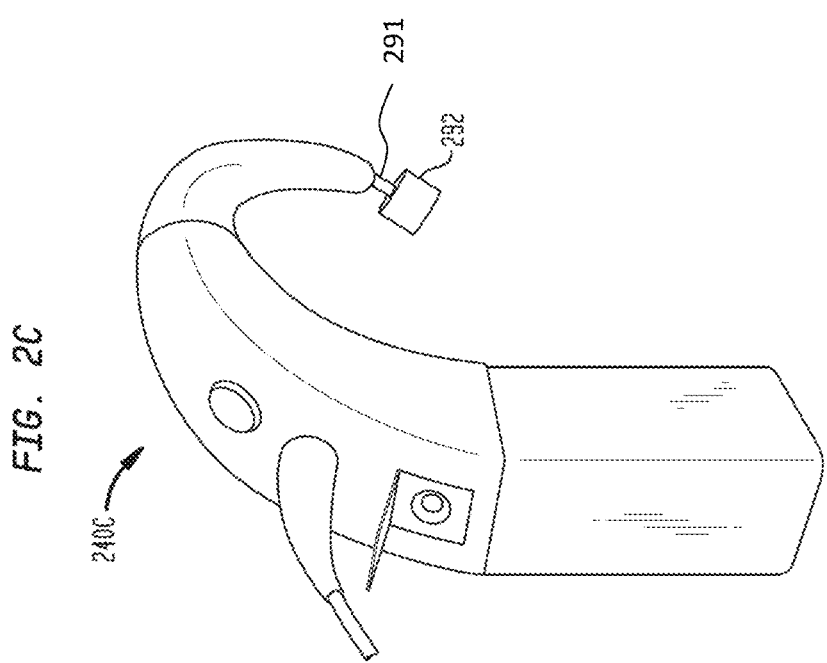

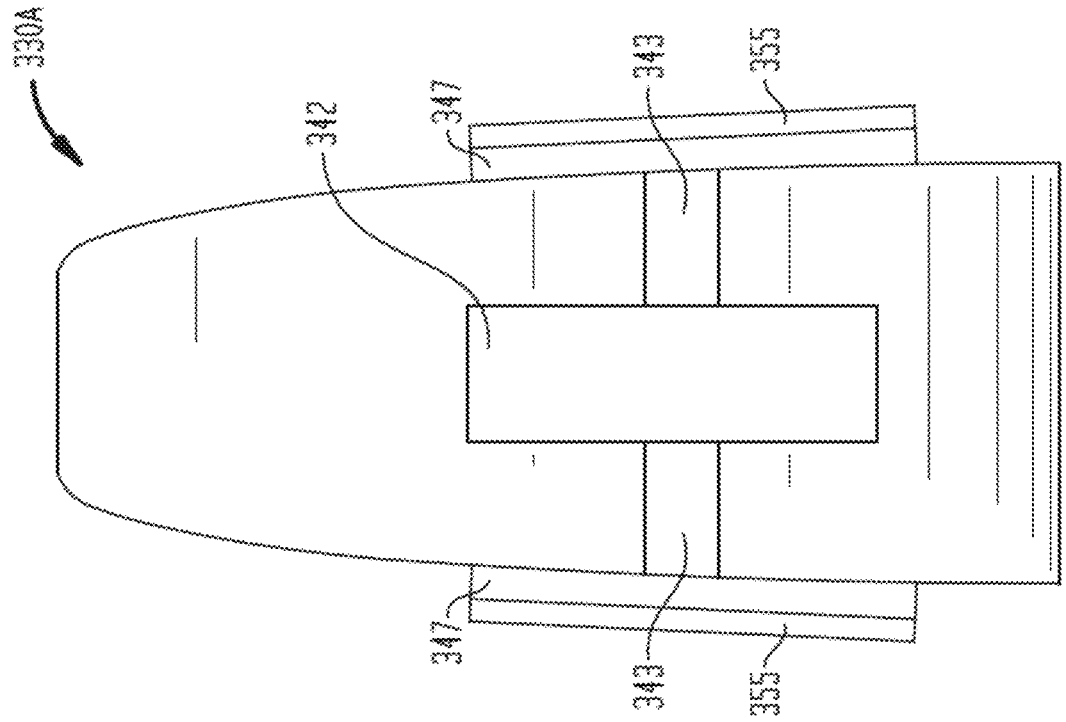

EXTERNAL DEVICE OF PROSTHESIS CONNECTOR

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient to bypass the mechanisms of the ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses a component positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, certain types of hearing prostheses, commonly referred to as bone conduction devices, convert a received sound into mechanical vibrations. The vibrations are transferred through the skull to the cochlea causing generation of nerve impulses, which result in the perception of the received sound. Bone conduction devices may be a suitable alternative for individuals who cannot derive sufficient benefit from acoustic hearing aids. Other types of hearing prostheses, such as cochlear implants and middle ear implants, can be a suitable alternative for individuals.

SUMMARY

In an exemplary embodiment, there is an external device of a prosthesis, such as a BTE device or a button sound processor device, comprising an electronics component; and a power component, removably attached to the electronics component, wherein the external device is configured with electrical current protection at a plug-socket arrangement connecting the power component to the electronics component.

In another exemplary embodiment, there is a behind-the-ear (BTE) device (or a button sound processor device, in some alternate embodiments), comprising an electronics component, and a power component, removably attached to the electronics component, wherein the BTE device is configured with an environmental barrier at the general interface between the electronics component and the power component.

In another exemplary embodiment, there is a behind-the-ear (BTE) device (or a button sound processor device, in some alternate embodiments), comprising a sound processor sub-assembly, and a battery sub-assembly, removably attached to the sound processor sub-assembly, wherein the BTE device is configured such that component(s) of the battery sub-assembly that enable the removable attachment to the sound processor sub-assembly will wear out before component(s) of the sound processor sub-assembly that enable removable attachment to the battery sub-assembly due to repeated removal and attachment of the battery sub-assembly from/to the sound processor sub-assembly.

BRIEF DESCRIPTION OF THE DRAWINGS

Embodiments of the present invention are described below with reference to the attached drawings, in which:

FIG. 2A is a perspective view of a Behind-The-Ear (BTE) device according to an exemplary embodiment;

FIG. 2C is a perspective view of an alternate embodiment of a BTE device;

FIG. 3A is a cross-sectional view of a spine of a BTE device according to an alternate embodiment;

DETAILED DESCRIPTION

The teachings detailed herein can be used as part of a BTE device or a device that includes a connector that is part of a partially implantable or a totally implantable cochlear implant. It is noted that in alternate embodiments, the teachings detailed herein and/or variations thereof can be applicable to other types of hearing prostheses, such as, for example, bone conduction devices (e.g., active transcutaneous bone conduction devices, passive transcutaneous bone conduction devices, and percutaneous bone conduction devices), Direct Acoustic Cochlear Implant (DACI), middle ear implants, etc. Embodiments can include any type of hearing prosthesis that can utilize the teachings detailed herein and/or variations thereof. It is further noted that in some embodiments, the teachings detailed herein and/or variations thereof can be utilized other types of prostheses beyond hearing prostheses. Thus, any disclosure herein corresponds to a disclosure of such used with/in any of the aforementioned devices.

Figure 1:
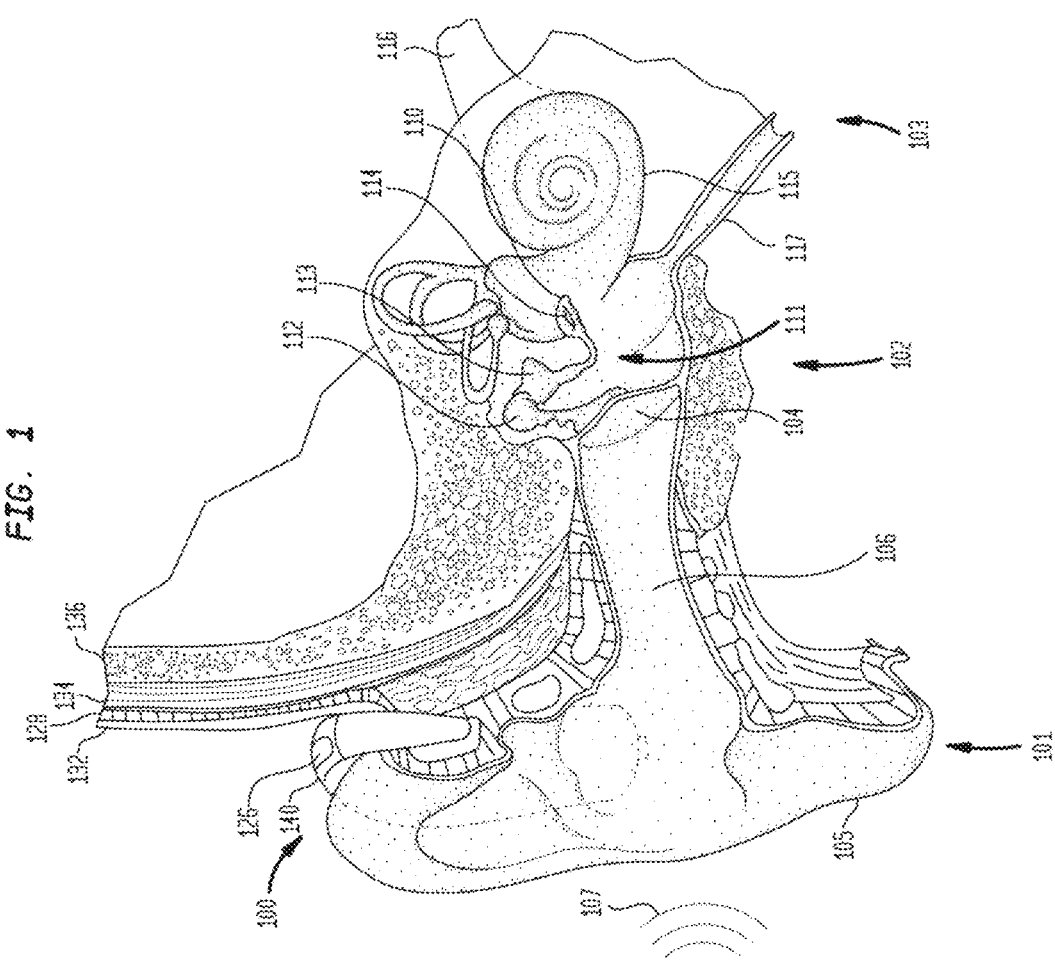
FIG. 1 is a perspective view of an exemplary bone conduction device in which embodiments of the present invention can be implemented.

FIG. 1 is a perspective view of a passive transcutaneous bone conduction device 100 in which embodiments of the present invention can be implemented, worn by a recipient. As shown, the recipient has an outer ear 101, a middle ear 102, and an inner ear 103. Elements of outer ear 101, middle ear 102, and inner ear 103 are described below, followed by a description of bone conduction device 100.

In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113, and the stapes 114. The ossicles 111 of middle ear 102 serve to filter and amplify acoustic wave 107, causing oval window 110 to vibrate. Such vibration sets up waves of fluid motion within cochlea 139. Such fluid motion, in turn, activates hair cells (not shown) that line the inside of cochlea 139. Activation of the hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102, and inner ear 103 of a recipient of device 100. As shown, bone conduction device 100 is positioned behind outer ear 101 of the recipient. Bone conduction device 100 comprises an external component 140 in the form of a behind-the-ear (BTE) device.

External component 140 typically comprises one or more sound input elements 126, such as microphone, for detecting and capturing sound, a sound processing unit/sound processor (not shown) and a power source (not shown). The external component 140 includes an actuator (not shown), which in the embodiment of FIG. 1, is located within the body of the BTE device, although in other embodiments, the actuator can be located remote from the BTE device (or other components of the external component 140 having a sound input element, a sound processing unit and/or a power source, etc.).

It is noted that sound input element 126 can comprise, for example, devices other than a microphone, such as, for example, a telecoil, etc. In an exemplary embodiment, sound input element 126 can be located remote from the BTE device and can take the form of a microphone or the like located on a cable or can take the form of a tube extending from the BTE device, etc. Alternatively, sound input element 126 can be subcutaneously implanted in the recipient, or positioned in the recipient's ear. Sound input element 126 can also be a component that receives an electronic signal indicative of sound, such as, for example, from an external audio device. For example, sound input element 126 can receive a sound signal in the form of an electrical signal from an MP3 player electronically connected to sound input element 126.

The sound processing unit/sound processor of the external component 140 processes the output of the sound input element 126, which is typically in the form of an electrical signal. The processing unit generates control signals that cause the actuator to vibrate. In other words, the actuator converts the electrical signals into mechanical vibrations for delivery to the recipient's skull.

As noted above, with respect to the embodiment of FIG. 1, bone conduction device 100 is a passive transcutaneous bone conduction device. That is, no active components, such as the actuator, are implanted beneath the recipient's skin 132. In such an arrangement, as will be described below, the active actuator is located in external component 140.

The embodiment of FIG. 1 is depicted as having no implantable component. That is, vibrations generated by the actuator are transferred from the actuator, into the skin directly from the actuator and/or through a housing of the BTE device, through the skin of the recipient, and into the bone of the recipient, thereby evoking a hearing percept without passing through an implantable component. In this regard, it is a totally external or non-surgical bone conduction device. Alternatively, in an exemplary embodiment, there is an implantable component that includes a plate or other applicable component, as will be discussed in greater detail below. The plate or other component of the implantable component vibrates in response to vibration transmitted through the skin.

FIG. 2A is a perspective view of a BTE device 240 of a hearing prosthesis, which, in this exemplary embodiment, corresponds to the BTE device (external component 140) detailed above with respect to FIG. 1. BTE device 240 includes one or more microphones 202, and may further include an audio signal jack 210 under a cover 220 on the spine 230 of BTE device 240. It is noted that in some other embodiments, one or both of these components (microphone 202 and/or jack 210) may be located on other positions of the BTE device 240, such as, for example, the side of the spine 230 (as opposed to the back of the spine 230, as depicted in FIG. 2), the ear hook 290, etc. FIG. 2A further depicts battery 252 and ear hook 290 removably attached to spine 230.

Figure 2B:
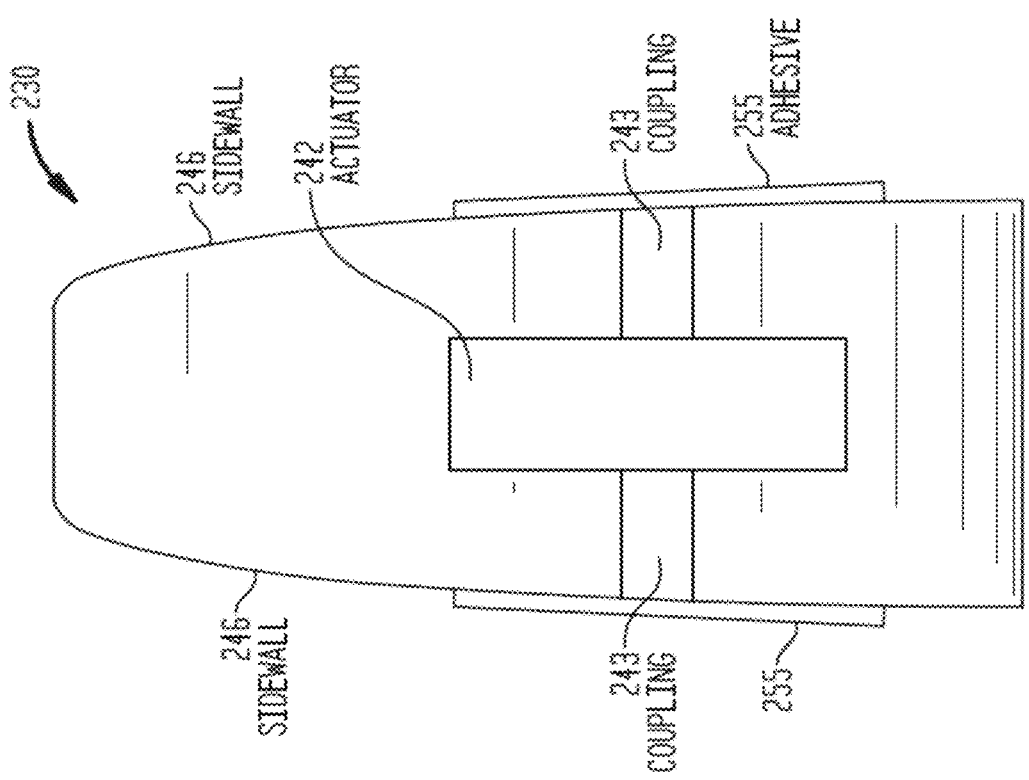
FIG. 2B is a cross-sectional view of a spine of the BTE device of FIG. 2A.

FIG. 2B is a cross-sectional view of an exemplary spine 230 of BTE device 240 of FIG. 2A. Actuator 242 is shown located within the spine 230 of BTE device 242. Actuator 242 is a vibrator actuator, and is coupled to the sidewalls 246 of the spine 230 via couplings 243 which are configured to transfer vibrations generated by actuator 242 to the sidewalls 246, from which those vibrations are transferred to skin 132. In an exemplary embodiment, couplings 543 are rigid structures having utilitarian vibrational transfer characteristics. The sidewalls 246 form at least part of a housing of spine 230. In some embodiments, the housing hermetically seals the interior of the spine 230 from the external environment.

In the embodiment of FIGS. 2A and 2B, the BTE device 240 forms a self-contained transcutaneous bone conduction device. It is a passive transcutaneous bone conduction device in that the actuator 242 is located external to the recipient.

FIG. 2B depicts adhesives 255 located on the sidewalls 246 of the BTE device 240. As will be detailed below, adhesives 255 form coupling portions that are respectively configured to removably adhere the BTE device 240 to the recipient via adhesion at the locations of the adhesives 255. This adherence being in addition to that which might be provided by the presence of the ear hook 290 and/or any grasping phenomenon resulting from the auricle 105 of the outer ear and the skin overlying the mastoid bone of the recipient. Accordingly, in an exemplary embodiment, there is an external component, such as a BTE device, that includes a coupling portion that includes a surface configured to directly contact the outer skin. This coupling portion is configured to removably attach the external component to an outer surface of skin of the recipient via attraction of the contact surface to the respective contact portion of the outer skin.

It is noted that the embodiment of FIG. 2B is depicted with adhesives 255 located on both sides of the BTE device. In an exemplary embodiment of this embodiment, this permits the adherence properties detailed herein, and/or variations thereof, to be achieved regardless of whether the recipient wears the BTE device on the right side (in accordance with that depicted in FIG. 1) or the left side (or wears two BTE devices). In an alternate embodiment, BTE device 240 includes adhesive only on one side (the side appropriate for the side on which the recipient intends to wear the BTE device 240). An embodiment of a BTE device includes a dual-side compatible BTE bone conduction device, as will be detailed below.

The adhesives 255 are depicted in FIG. 2B in an exaggerated manner so as to be more easily identified. In an exemplary embodiment, the adhesives 255 are double sided tape, where one side of the tape is protected by a barrier, such as a silicone paper, that is removed from the skin-side of the double-sided tape in relatively close temporal proximity to the placement of the BTE device 240 on the recipient. In an exemplary embodiment, adhesives 255 are glue or the like. In an exemplary embodiment where the adhesives 255 are glue, the glue can be applied in relatively close temporal proximity to the placement of the BTE device 240 on the recipient. Such application can be applied by the recipient to the spine 230, in an exemplary embodiment.

In an alternate embodiment, the adhesives 255 are of a configuration where the adhesive has relatively minimal adhesive properties during a temporal period when exposed to some conditions, and has relatively effective adhesive properties during a temporal period, such as a latter temporal period, when exposed to other conditions. Such a configuration can provide the recipient control over the adhesive properties of the adhesives.

By way of example, the glue and/or tape (double-sided or otherwise) may be a substance that obtains relatively effective adhesive properties when exposed to oil(s) and/or sweat produced by skin, when exposed to a certain amount of pressure, when exposed to body heat, etc., and/or a combination thereof and/or any other phenomena that may enable the teachings detailed herein and/or variations thereof to be practiced. Such exemplary phenomena may be, for example, heat generated via friction resulting from the recipient rubbing his or her finger across the glue. In an exemplary embodiment, the pressure can be a pressure above that which may be expected to be experienced during normal handling of the spine 230.

In an exemplary embodiment, the adhesives 255 are contained in respective containers that exude glue or the like when exposed to certain conditions, such as by way of example and not by way of limitation, the aforementioned conditions. Alternatively, and/or in addition to this, the recipient may puncture or otherwise open the containers to exude the glue or the like.

Any device, system, and/or method that will enable a recipient to practice the teachings detailed herein and/or variations thereof associated with the adherence of the bone conduction device to skin of the recipient for vibration transmission can be utilized in some embodiments.

In an exemplary embodiment, the vibrator actuator 242 is a device that converts electrical signals into vibration. In operation, sound input element 202 converts sound into electrical signals. Specifically, these signals are provided to vibrator actuator 242, or to a sound processor (not shown) that processes the electrical signals, and then provides those processed signals to vibrator actuator 242. The vibrator actuator 242 converts the electrical signals (processed or unprocessed) into vibrations. Because vibrator actuator 242 is mechanically coupled to sidewalls 246, the vibrations are transferred from the vibrator actuator 342 to skin 132 of the recipient.

FIG. 2A depicts the sound input element 202 as being located at about the apex of spine 230. FIG. 2C depicts an alternate embodiment of a BTE device 240C in which the sound input element 292 is mounted on a stem 291 extending from the ear hook 290. In an exemplary embodiment, the stem 291 is such that during normal use, the sound input element 292 is located below the ear, in the area of the auricular concha, or in the ear canal. Such a configuration can have utilitarian value by way of reducing feedback as compared to that which may result from the embodiment of FIG. 2A.

It is noted that while the embodiments depicted in FIGS. 2A and 2B detail the vibrations being transferred from the vibrator actuator 242 to the sidewalls 246 via the couplings 243, in other embodiments, the vibrations are transferred to plates or other devices that are located outside of the sidewalls 246. FIG. 3A depicts such an exemplary embodiment, where spine 330A includes couplings 343 extending through sidewalls 346 to plates 347, on which adhesives 355 are located.

Figure 3B:
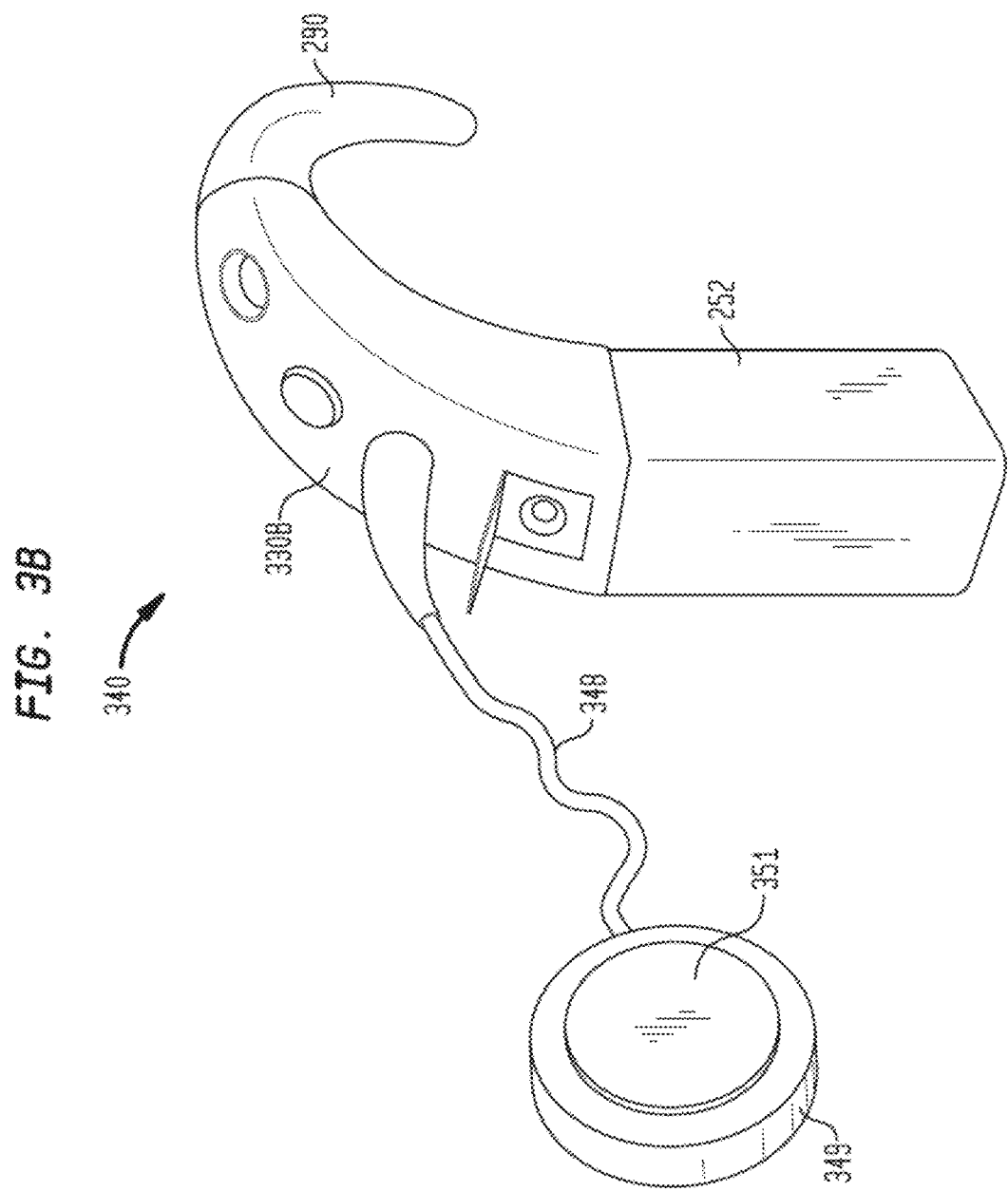
FIG. 3B is a perspective view of an alternate embodiment of an external device including a BTE device.

FIG. 3B depicts an alternate embodiment of an external component of a bone conduction device, BTE device 340, in which the vibrator actuator (such as actuator 242 detailed above, or a variation thereof) is located in a remote vibrator actuator unit 349 (sometimes referred to as a "button" in the art). This as opposed to the spine 330B. Vibrator actuator unit 349 is in electronic communication with spine 330B via cable 348. Spine 330B functionally corresponds to the spines detailed above, with the exception of the features associated with containing a vibrator actuator therein. In this regard, electrical signals are transferred to the vibrator actuator in vibrator actuator unit 349, these signals being, in some embodiments, the same as those which are provided to the other vibrator actuators detailed herein. Vibrator actuator unit 349 may include a coupling 351 to removably attach the unit 349 to outer skin of the recipient. Coupling 351 can correspond to the couplings detailed herein. Such a coupling may include, for example, adhesive. Alternatively, and/or in addition to this, coupling 351 can correspond to a magnet that couples via magnetic attraction to an implanted magnet within the recipient (e.g., an implanted magnet attached to the mastoid bone of the recipient underneath the skin of the recipient).

Such a configuration as that of BTE device 340, can have utilitarian value by way of reducing feedback as compared to that which may result from the embodiment of FIG. 2A.

While the embodiment depicted in FIG. 3B utilizes a cable 348 to communicate with the remote vibrator actuator unit 349, in an alternative embodiment, a wireless link is utilized to communicate between the spine 330B and the remote vibrator actuator unit 349.

In at least some exemplary embodiments, the remote vibrator actuator unit 349 can contain a sound processor/ sound processing unit or the like as opposed to, and/or in addition to, the spine 330B. Accordingly, in an exemplary embodiment, the remote vibrator actuator unit 349 can be a button sound processor, where, in at least some embodiments, the functionality of the BTE device vis-à-vis sound capture and/or signal processing and/or power is instead present in the button sound processor, enabling, in at least some exemplary embodiments, the BTE device to be done away with.

It is noted that while the embodiment of FIG. 3B depicts the microphone being located on the spine 330B at about the apex thereof, in an alternate embodiment, the microphone can be located in a manner corresponding to that of FIG. 2C. It is further noted that the microphone can be located on the ear hook 290 anywhere from and including the tip thereof to the location where the ear hook interfaces with the spine. Such is also the case with respect to the microphone located on the spine 330B—the microphone can be located anywhere on the spine from the interface of the spine in the ear hook 290 to the interface of the battery 252 with the spine 330B. Still further, as noted above, BTE device 340 can include a plurality of microphones located according to the various teachings detailed herein and/or variations thereof. In this regard, the aforementioned locations of the various microphones are applicable to the other embodiments detailed herein, such as by way of example, the embodiment of FIG. 2A, along with the embodiments that will be detailed below. Any microphone placement that can enable the teachings detailed herein and/or variations thereof to be practiced can be utilized in at least some exemplary embodiments.

In some exemplary embodiments, any device, system, and/or method that will enable the teachings detailed herein and/or variations thereof associated with vibration transmission from the actuator to the skin and/or to bone of the recipient may be utilized.

It is briefly noted that in an exemplary embodiment, the arrangement of FIG. 3B can instead be that of a cochlear implant external component/removable component, or a middle ear implant external component/removable component, or an active transcutaneous bone conduction device external component/removable component, where element 349 is an RF inductance coil that transcutaneously communicates via inductance with an implanted RF inductance coil that is in signal communication with a stimulator when actuator alike of the implantable component.

It is noted that the teachings herein can be applied to any of a variety of auditory prostheses/auditory prosthesis components in accordance with the embodiments herein.

Accordingly, application of the concepts herein are limited to the explicit examples discussed. Again, while the above has tended to focus on bone conduction, the teachings can be applicable to a middle ear implant where an RF coil is in wired communication with the BTE device, which RF coil transcutaneously transmits power and/or control signals to an implanted RF coil of the implanted component to cause the implanted actuator to vibrate, a cochlear implant where again, an RF coil is in wired communication with the BTE device, which RF coil transcutaneously transmits power and/or control signals to an implanted RF coil of the implanted component to cause the implanted component to provide electrical stimulation to the cochlea, as well as active transcutaneous bone conduction devices using the RF coil regime just described, or passive transcutaneouls bone conduction devices where the vibrator is in the BTE or remote from the BTE via a wire, or percutaneous bone conduction device, where the vibrator is in wired communication with the BTE to power the vibrator. Indeed, the teachings herein can also be used for a retinal prosthesis, or other types of prostheses.

Also, the battery connection could be applied to a button sound processor or the like, where there is no BTE device, or to other types of external components, such as a button sound processor where there is also a BTE device. Accordingly, any disclosure herein with respect to a BTE device also corresponds to a disclosure of a button sound processor device. In this regard, in an exemplary embodiment, any disclosure herein of the sound processor subassembly and/or the electronics component subassembly of a BTE device also corresponds to the sound processor subassembly and/or the electronics component of a button sound processor, and any disclosure herein of the power subcomponent and/or the battery component of a BTE device also corresponds to the power subcomponent and/or the battery component of a button sound processor. To be clear, a button sound processor is known in the art is a component that is self-contained in that it includes microphones and sound processing components and RF communication components and a power component all as part of a button that in at least some exemplary embodiments, magnetically couples to the implanted component so as to communicate via an RF signal to the implantable component. It is called a button sound processor because it resembles a button when held against the skin of the recipient. In at least some exemplary embodiments, there are no electrical leads or the like extending therefrom to, for example, a BTE device.

Some additional embodiments of some exemplary embodiments will now be described.

Figure 4:
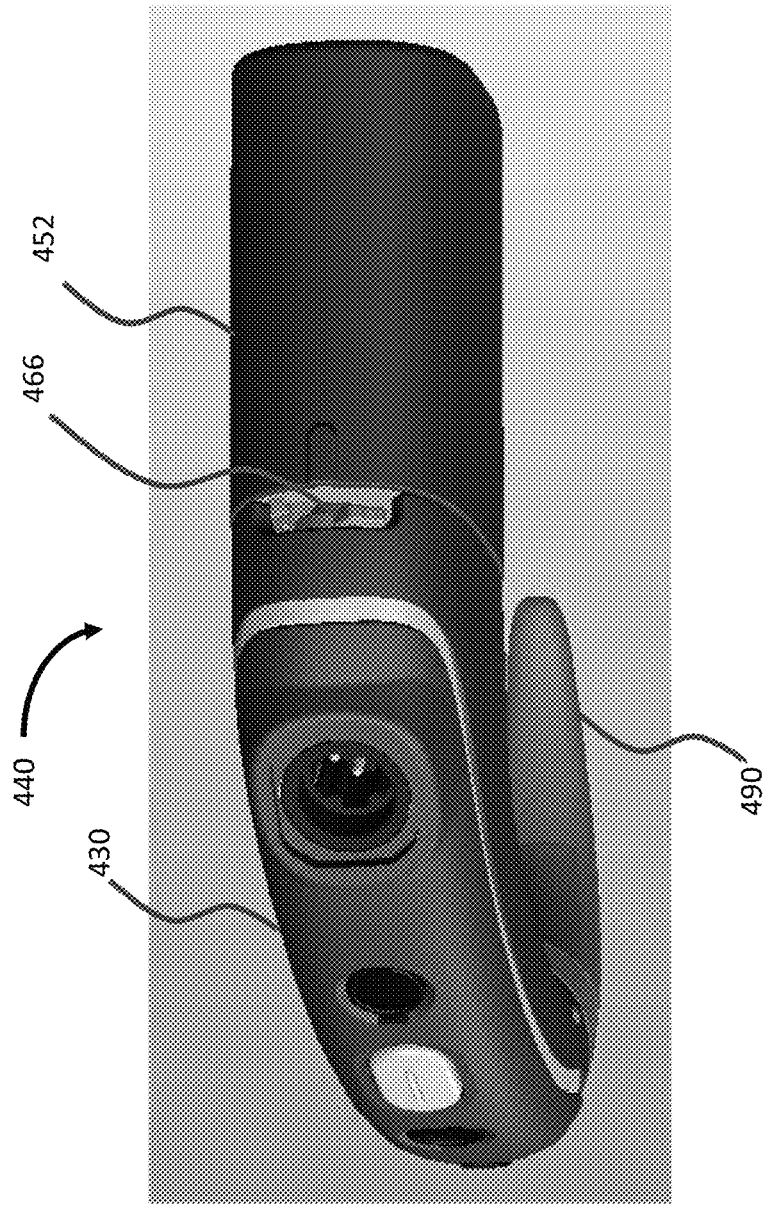
FIG. 4 is a perspective view of an alternate embodiment of a BTE device.

FIG. 4 depicts an exemplary BTE device 440 according to an exemplary embodiment. As seen BTE device 440 includes element 430, which functionally and structurally can correspond to element 330B above, and thus corresponds to the spine of the BTE device. However, hereinafter, element 440 will be referred to by its more generic name as the signal processor sub-assembly, or sometimes the electronics component of the BTE device, or sometimes, for short, the signal processor. As can be seen, attached thereto is an element 452 which corresponds to element 252 above, and thus corresponds to a power component of the BTE device, which in some instances herein will be referred to as the battery sub-assembly, or the battery for short. Element 490 is an ear hook, and corresponds to element 290 above. The battery sub-assembly 452 is removably attached to the sound processor sub-assembly 430 via a bayonet connector, the details of which will be described below. Latch 466 enables the recipient to unlock and lock the battery sub-assembly 452 from and to, respectively, the sound processor sub-assembly 430, via moving the handle of the latch 466 from one side of the BTE device 440 to the other side of the BTE device 440.

Figure 5:
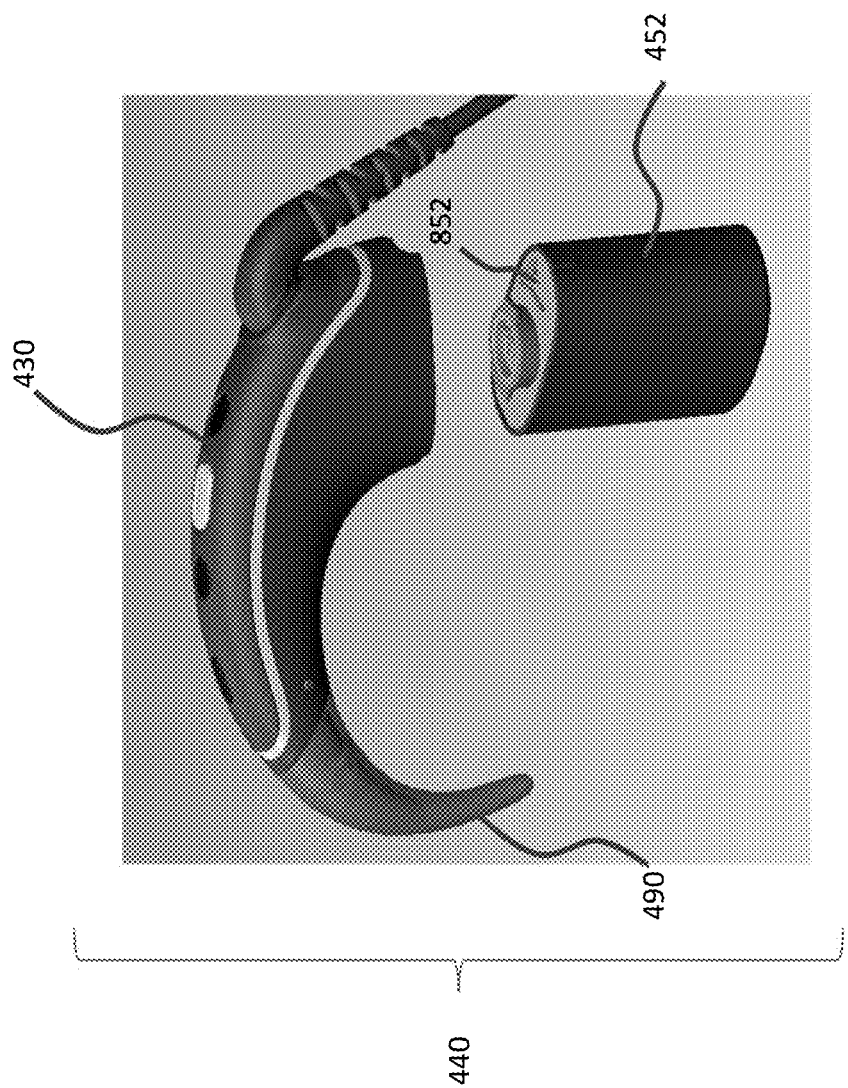
FIGS. 5, 6, and 7 are perspective views of attachment of a battery sub-assembly to a sound processor sub-assembly according to an exemplary embodiment.

FIG. 5 depicts the sound processor sub-assembly 430 and components connected thereto decoupled or otherwise unattached to the battery sub-assembly 452. The plug assembly 852 can be seen as part of the battery sub-assembly 452, which plug assembly interfaces with a corresponding socket assembly (not viewable in FIG. 5) of the electronics component 430 of the BTE device.

Figure 6:
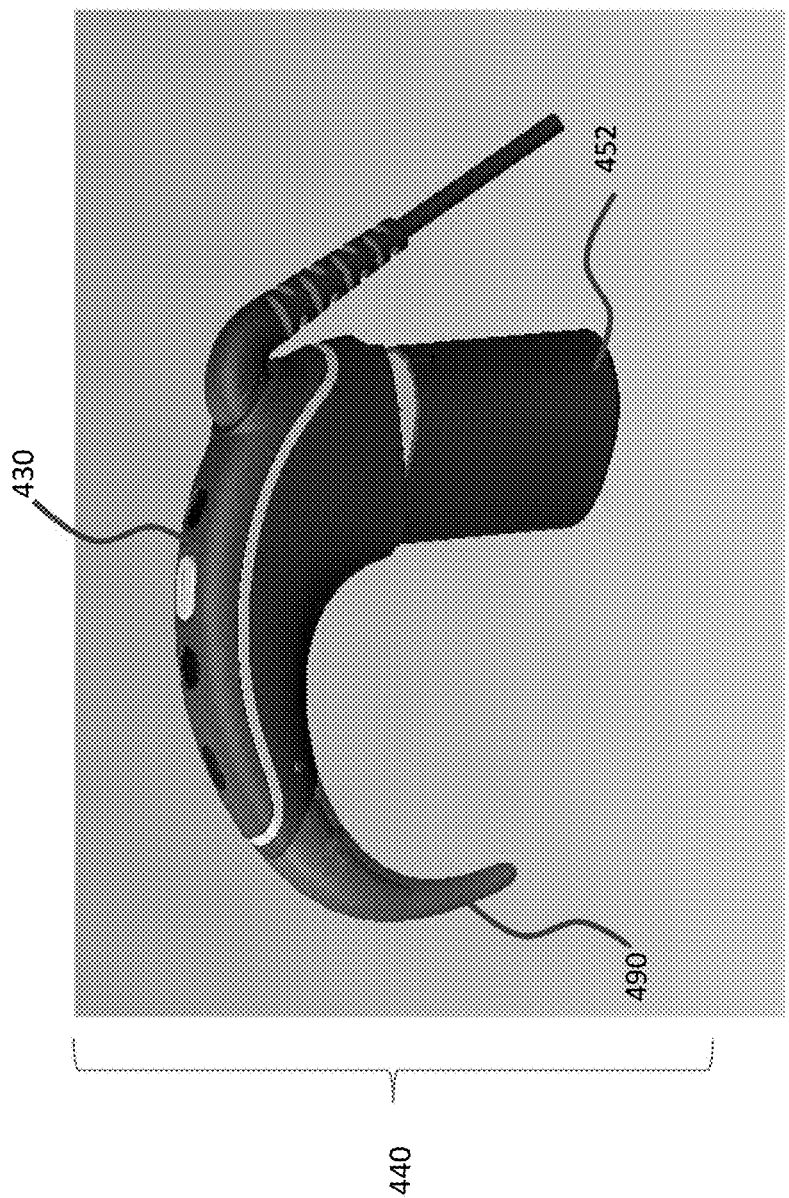
Figure 7:
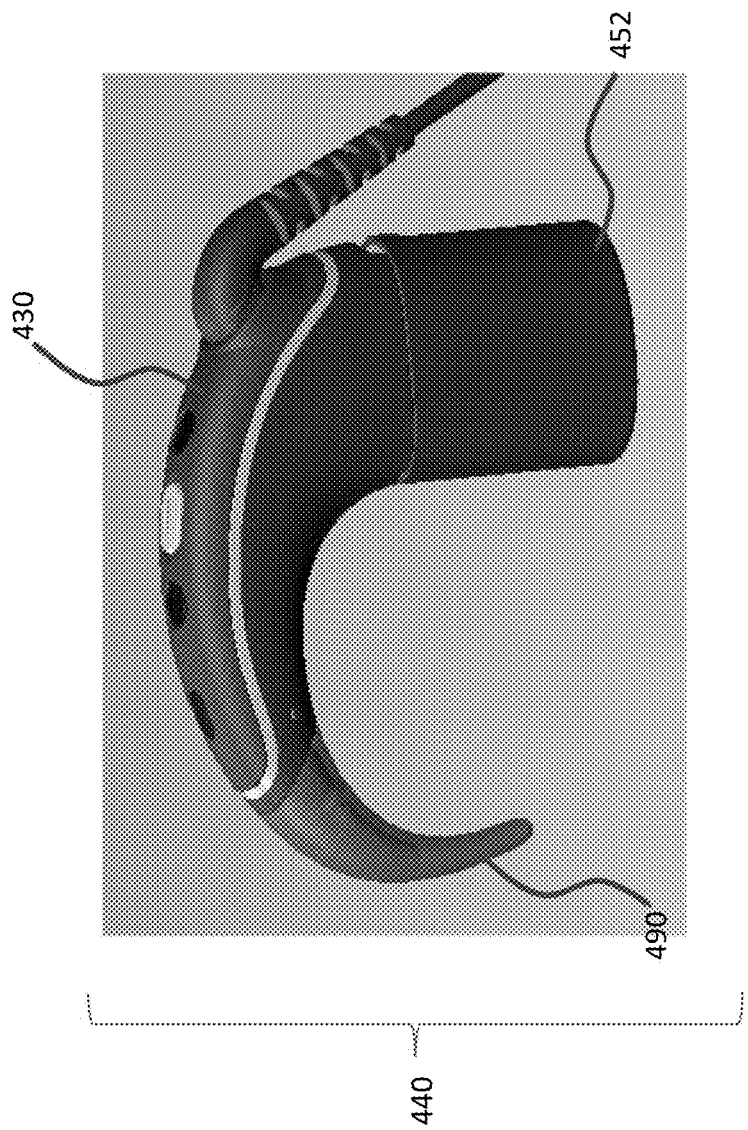

In an exemplary embodiment of attachment of the battery sub-assembly 452 to the sound processor sub-assembly 430, a recipient grasps the respective components with his or her left-hand and right-hand respectively, or vice versa, and moves the battery assembly 452 towards the sound processor sub-assembly 430, with the battery sub-assembly 452 canted about the longitudinal axis thereof relative to its final orientation when fully and completely attached to the sound processor sub-assembly 430. FIG. 6 depicts the battery sub-assembly 452 in contact with the sound processor sub-assembly 430 with some rotation about the longitudinal axis of the battery sub-assembly relative to that which is the case shown in FIG. 5. In an exemplary embodiment, this rotation engages the bayonet fittings to attach the battery sub-assembly 452 to the sound processor sub-assembly 430, as will be described in greater detail below. FIG. 7 depicts the battery sub-assembly 452 fully rotated about its longitudinal axis so as to fully connect or otherwise seat the battery sub-assembly 452 to/against the sound processor assembly 430. Subsequent this action, as noted above, the latch 466 is moved so as to lock the battery sub-assembly 452 to the sound processor sub-assembly 430. In an exemplary embodiment, to remove the battery sub-assembly 452 from the sound processor sub-assembly 430, the latch 466 is moved so as to unlock the components and then the battery sub-assembly 452 is rotated about its longitudinal axis so as to undo the bayonet fitting, and then put downward in the direction of its longitudinal axis, away from the sound processor sub-assembly 430, and thus decoupling the battery sub-assembly 452 from the sound processor sub-assembly 430.

Figure 8:
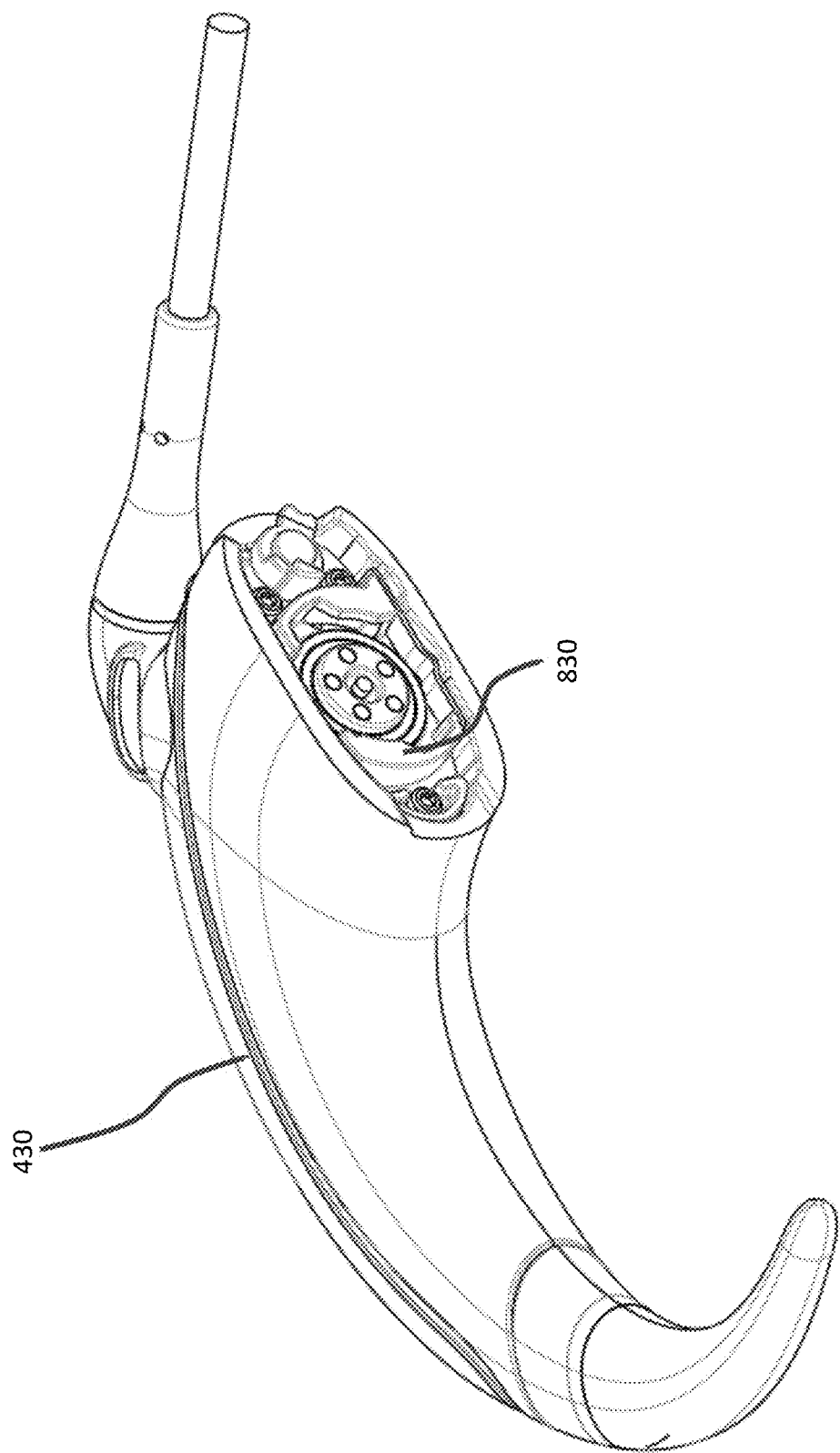
FIG. 8 is a bottom perspective view of a sound processor subassembly according to an exemplary embodiment.
Figure 9:
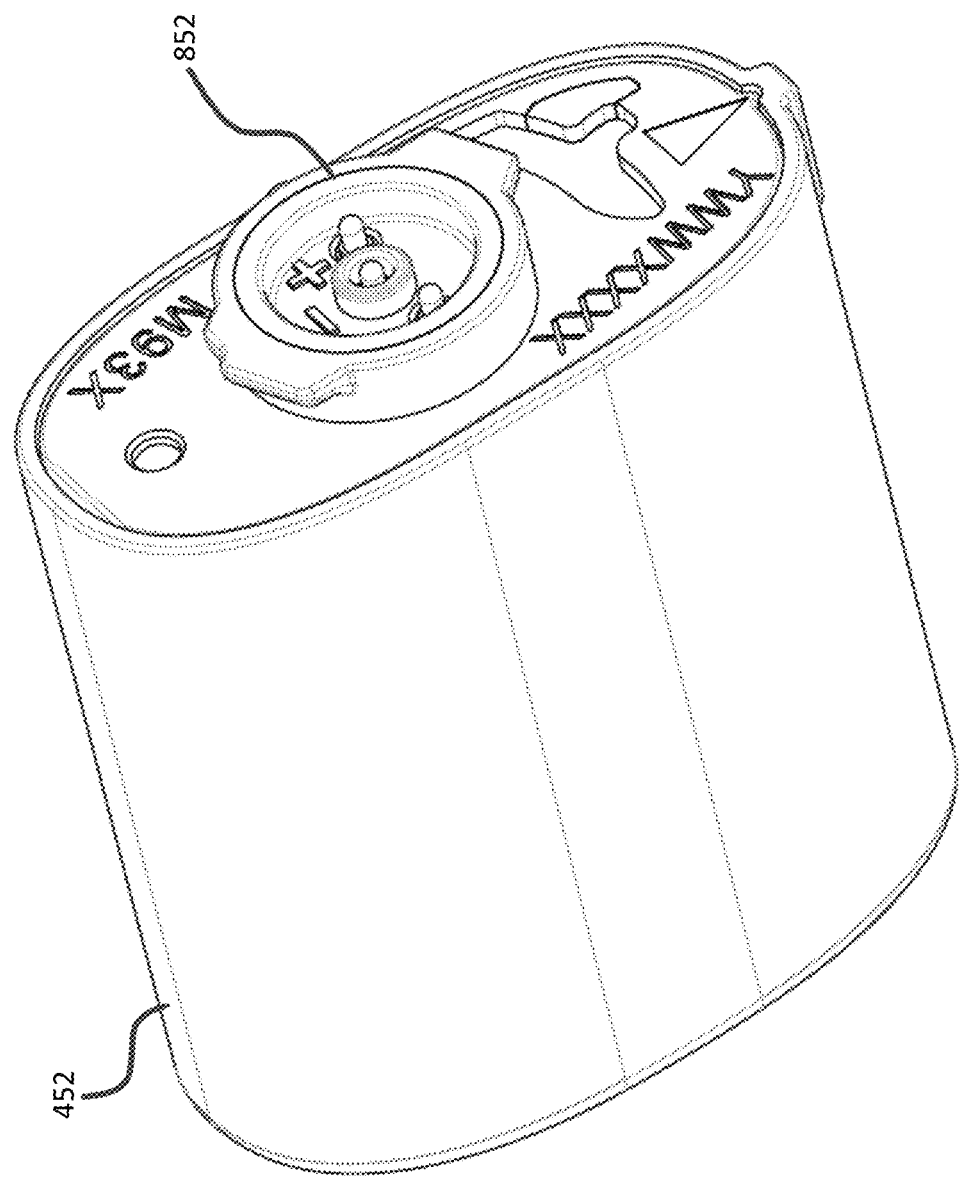
FIG. 9 is a top perspective view of a battery subassembly according to an exemplary embodiment.
Figure 10:
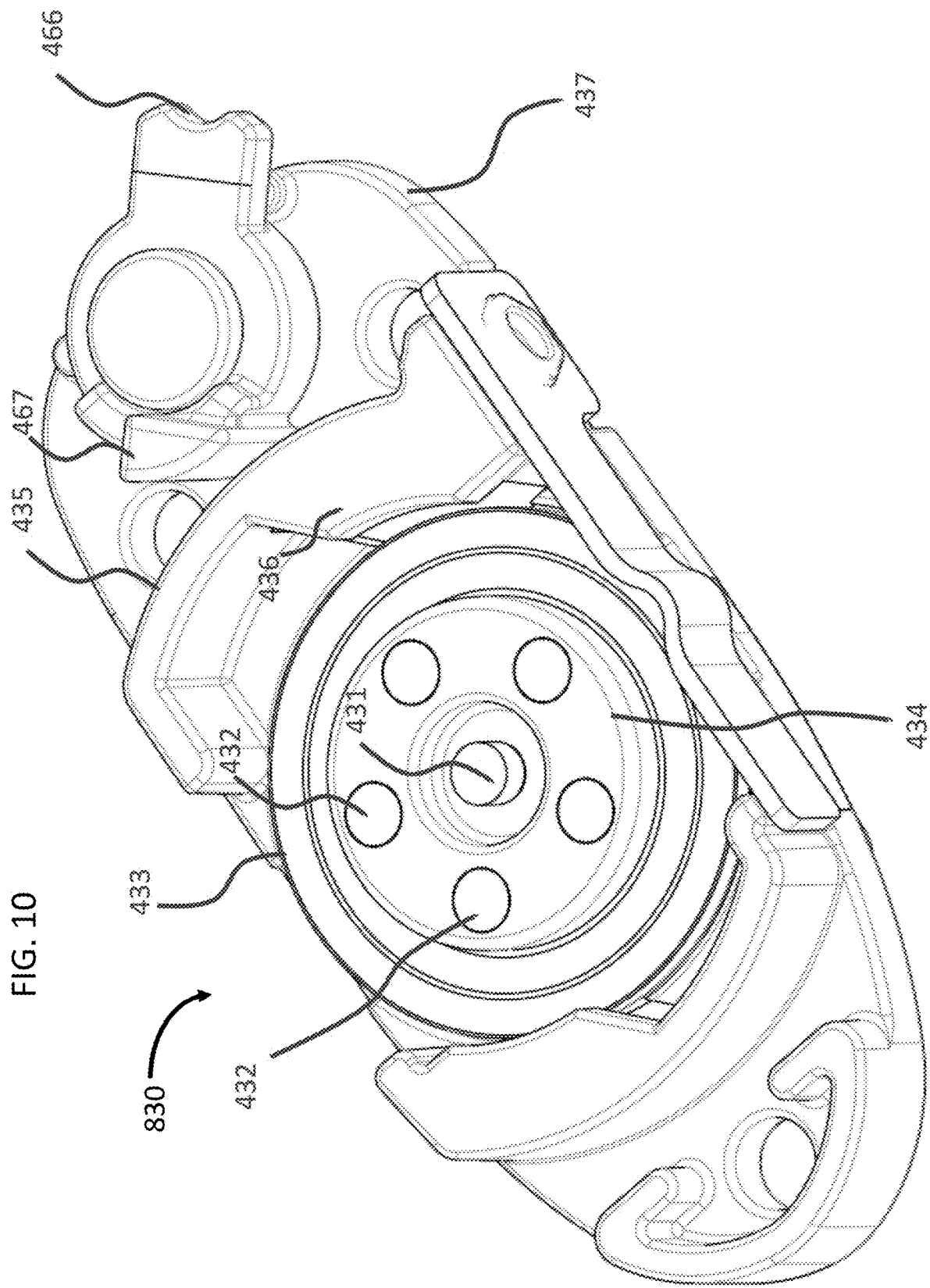
FIG. 10 is a perspective view of a socket assembly according to an exemplary embodiment.
Figure 11:
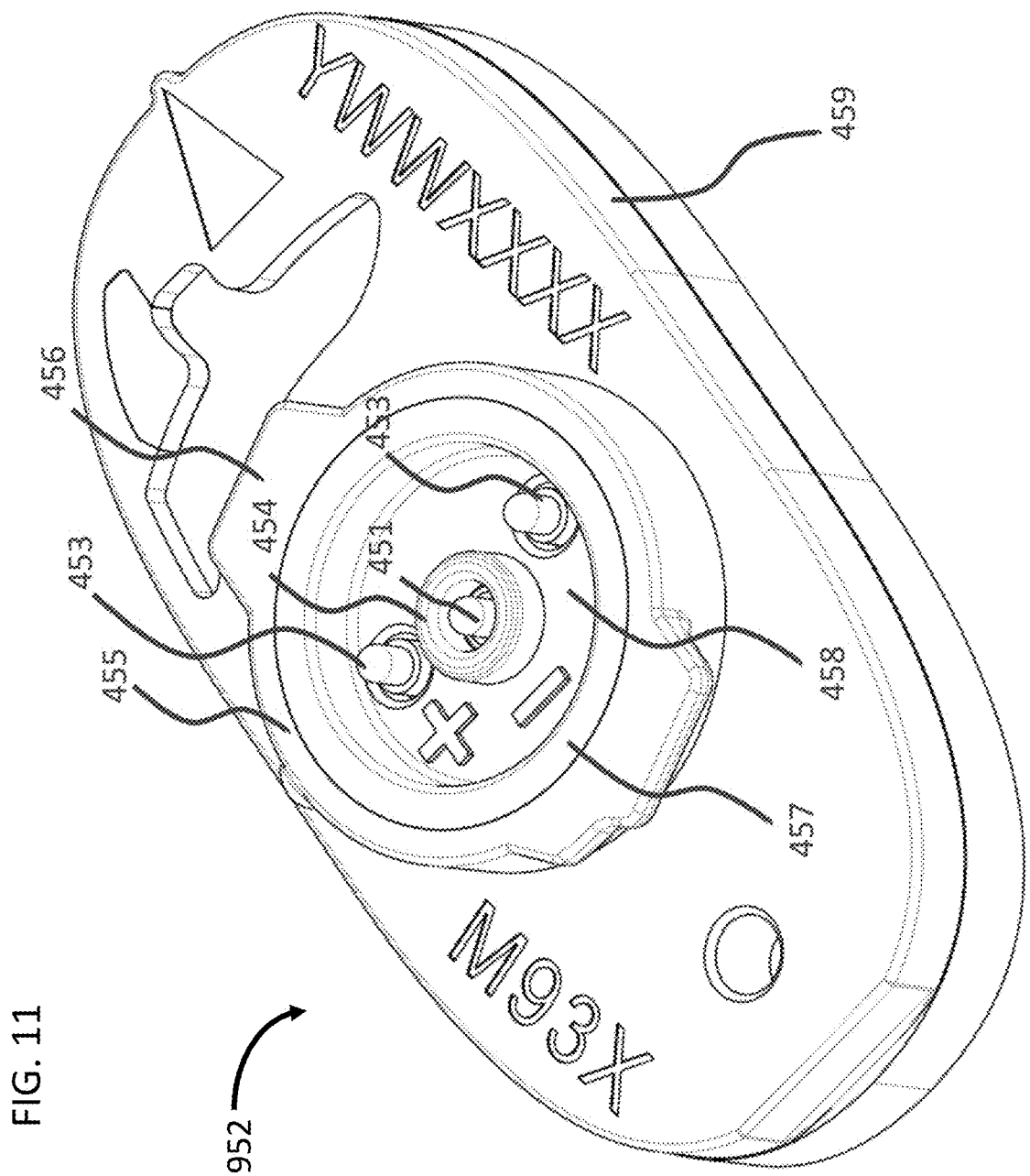
FIG. 11 is a perspective view of a plug assembly according to an exemplary embodiment.

FIG. 8 depicts an isometric bottom view of the sound processor sub-assembly 430 which enables a view of the socket assembly 830 thereof. FIG. 9 depicts an isometric top view of the battery sub-assembly 452 which depicts the plug assembly 852 thereof. As noted above, the plug 852 and the socket 830 respectively cooperate to form a bayonet coupling/bayonet connector. FIGS. 10 and 11 respectively depict the socket assembly 830 and the plug assembly 852 in isolation from the rest of the sound processor sub-assembly and the battery sub-assembly.

FIG. 10 depicts contacts 431 and 432, the latter contacts being arrayed in a planetary fashion about the sun like contact 431. In an exemplary embodiment, contact 431 is configured to be placed into electrical contact with the negative terminal of the battery sub-assembly 452. Contacts 432 are variously respectively configured to be placed into electrical contact with the positive terminal(s) of the battery sub-assembly 452. It is briefly noted that while only one contact 431 and only five contacts 432 are depicted, in some embodiments, there can be more than one contact 431 and more than five contacts 432, or fewer than five contacts 432. Any arrangement that can enable the teachings detailed herein can be utilized in at least some exemplary embodiments. The contacts 431 and 432 are arrayed and otherwise extend through a plastic contact pad retainer 434, as can be seen. In an exemplary embodiment, the plastic contact pad retainer 434 includes a depression in the center thereof in which contact 431 is located, as can be seen. Here, contact 431 is proud of the outwardly facing surface of the plastic contact pad retainer 434. Conversely, contacts 432 are flush with the outwardly facing surface of the contact pad retainer 434. In an exemplary embodiment, the ends of the contacts 431 and 432 are flush with each other, while in alternative embodiments, the ends can be located at different heights relative to each other. In an exemplary embodiment, the contact 431 and 432 are fixed relative to each other and relative to the plastic contact pad retainer 434. However, in some alternate embodiments, the contacts 431 and/or 432, at least one or more of them, are spring-loaded or otherwise enable to move in the longitudinal direction of the socket assembly 830.

FIG. 10 depicts part of the female portion of the bayonet coupling 435, which has wings 436 that overhang cavities into which wings of the bayonet coupling of the plug enter upon rotation of the plug/battery sub assembly, as will be described in greater detail below. In any event, as can be seen, the wings 436 extend only part of the way across the lateral axis of the socket assembly 830, thus providing a space into which the wings 456 of bayonet coupling of the plug can be fitted so as to achieve the longitudinal location of the battery sub-assembly relative to the sound processor sub-assembly, after which rotation about the longitudinal axis moves the wings 456 from the space to the cavities over which the wings 436 extend, thereby removably coupling the battery sub-assembly to the sound processor sub-assembly.

Still with reference to FIG. 10, as can be seen, the socket assembly 830 includes what can be generally referred to as a chassis 437 which faces downward at the bottom of the sound processor sub-assembly 430, and otherwise supports the other components of the socket assembly. Also seen in FIG. 10 is a seal apparatus 433 which is configured to provide a fluidic barrier against fluidic intrusion from the ambient environment into the inboard area of the seal 433 in general, and to the contacts 431 and/or 432 in particular, when the seal apparatus 433 interacts with the corresponding component(s) of the plug 952, as will be detailed below.

In an exemplary embodiment, the chassis 437 is made of titanium-based materials. That said, in an alternative embodiment, in at least some instances, the chassis 437 can be made of plastic or other types of polymers. It is also noted that in at least some exemplary embodiments, the chassis 437 is plated or otherwise coated with nickel or a nickel alloy or nickel-PTFE, at least in the locations which interface with the plug assembly in general, and the components that enable the removable attachment of the plug to the socket in particular. Additional details of this will be described in greater detail below.

Lever 466 can be seen in FIG. 10. In this embodiment, the lever is a monolithic component with the lock component 467 that locks the battery sub-assembly to the sound processor sub-assembly upon movement thereof, and unlocks the battery sub-assembly from the sound processor sub-assembly upon movement thereof in the opposite direction. Other configurations can be utilized, such as a non-monolithic lock. Indeed, in some embodiments, there is no lock, instead friction and the like is relied upon to hold the sub-assemblies in place.

FIG. 11 depicts the plug assembly 952. The plug assembly 952 includes a chassis 459 which can be made out of plastic in some embodiments, and can be made out of a titanium metal in other embodiments. The plug includes contacts 451 and 453. Contact 451 is a negative contact of the battery, and contacts 453 are positive contacts. While only two contacts 453 are depicted, in some alternate embodiments, only one contact 453 is present, while in other embodiments, more than two contacts 453 are present. Further, while only one contact 451 is depicted, in some alternate embodiments, two or more contacts 451 are present. The contacts 451 and 453 are spring-loaded or otherwise biased in the upward/extended position. In an exemplary embodiment, upon contact of the contacts 451 and 453 with the socket assembly components, and subsequent movement of the battery sub-assembly towards the sound processor sub-assembly, the socket components push the contacts 451 and 453 downward/to a retracted state/inward into the plug assembly. That said, in some alternate embodiments, the contacts 451 and/or 453, at least one or more of them, are fixed relative to the chassis 459 with respect to all three axes of movement. In at least some exemplary embodiments, at least in the unrestrained state, the tips of the contact 453 and 451 are located at the same height relative to one another. In at least some exemplary embodiments, when the battery sub-assembly is fully connected to the sound processor sub-assembly, the tips of the contacts 453 and 451 remain located at the same height relative to one another, albeit at a height that may be lower than that which was the case in the relaxed state/extended state before the battery sub-assembly was mated with the sound processor sub-assembly. That said, in some alternate embodiments, the heights of the tips of one or more of the contacts 451 can be different with respect to each other and/or with respect to one or more of the tips of the contact 453, and vice versa.

The male portion of the bayonet coupling 455 includes wings 456 which interface with the wings of the socket assembly as detailed above so as to removably couple the battery sub-assembly to the sound processor sub-assembly. In an exemplary embodiment, the male portion of the bayonet coupling 455 is made out of titanium or a titanium alloy. In an exemplary embodiment, the male portion can be made out of plastic or another polymer. In an exemplary embodiment, the male portion of the bayonet coupling 455 can be a titanium-based body coated with or otherwise plated with nickel or a nickel alloy or nickel-PTFE, at least with respect to those components that come into contact with the corresponding bayonet coupling components of the socket assembly.

As can be seen, there is a barrier extending about the negative contact 451 which extends upward out of the basin 458 inside the male coupling component(s) of the plug assembly 952. In an exemplary embodiment, this barrier is a rib that extends 360° about contact 451, and is a monolithic component of the chassis 459, although in other embodiments, the chassis 459 is not monolithic, but instead an assembly of components. Also as can be seen is a rib 457 that can also be a monolithic component of the chassis 459 which extends about the contacts 453 and extends coaxially with the rib 454 and with the contact 451. It is noted that in other embodiments, the rib 454 is a separate component from the chassis 459 (e.g., interference fitted, thereto, snap coupled thereto, etc.) In the embodiment depicted in FIG. 11, the male portion of the bayonet coupling extends about the rib 457. While the embodiments of elements 457 and 454 have been presented in terms of those components elements being ribs, in some alternate embodiments, other configurations can be the case as will be briefly described below.

Figure 12:
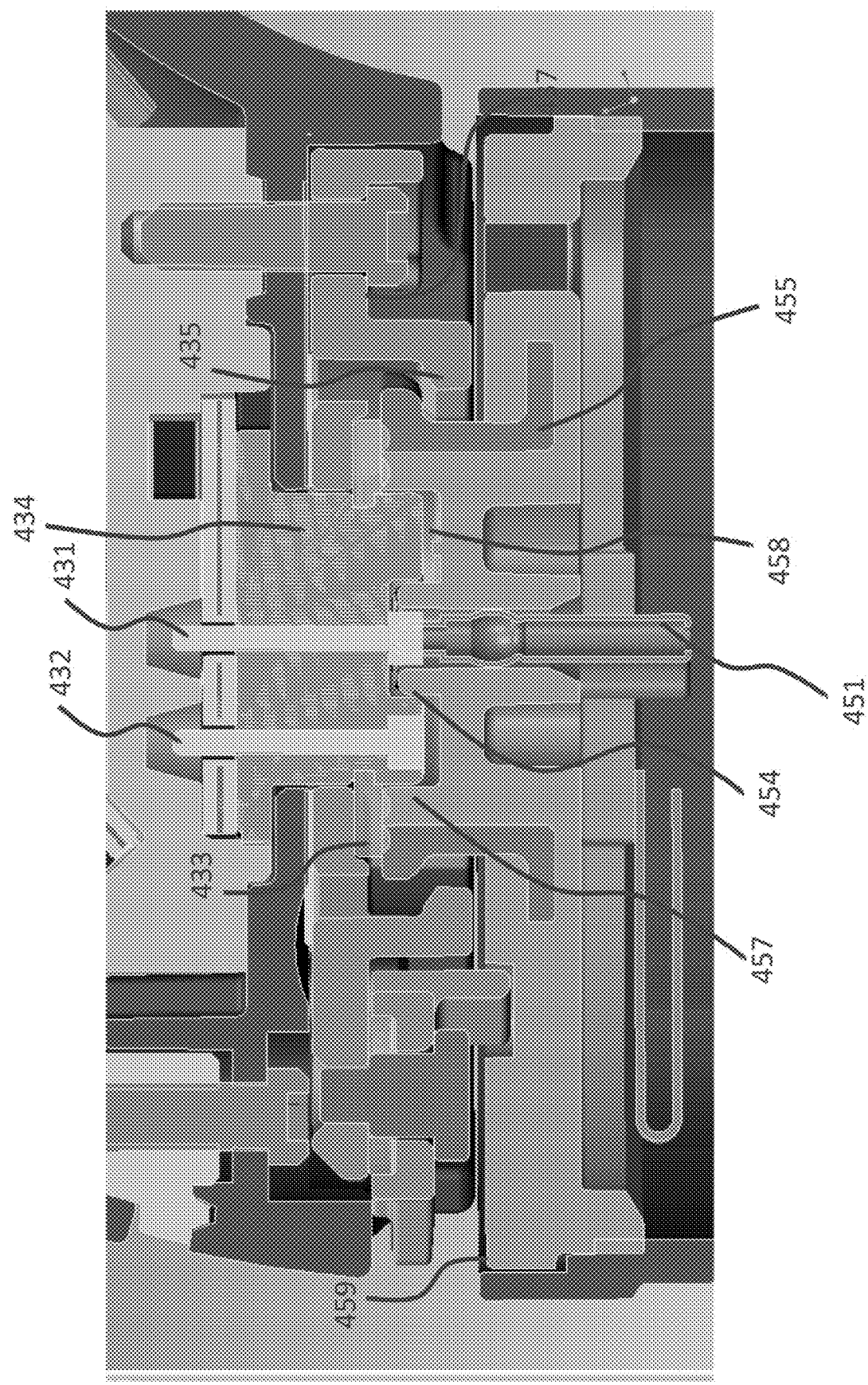
FIG. 12 is a cross-sectional view of a portion of a BTE device according to an exemplary embodiment.

FIG. 12 depicts a cross-sectional view along the longitudinal axis of the BTE device lying on a plane that is parallel to the major lateral axis of the BTE device (e.g., the plane normal to the page of FIG. 3A, where the plane of that page corresponds to the minor lateral axis of the BTE device). It is briefly noted that contact number 451 is depicted in a non-retracted state (i.e., it is depicted in its extended state), to demonstrate the amount of movement that would otherwise occur upon the coupling of the sound processor sub assembly the battery sub-assembly, and also to depict the relative weight of the tip of the contact 451 relative to the other components when the contact 451 is in the relaxed/extended state. Thus, it is to be understood that in actuality, contact 451 would be located downward on the y-axis of FIG. 12 further than that which is depicted to be the case in FIG. 12 upon coupling of the battery sub-assembly to the sound processor sub-assembly.

In view of the above, it can be seen that in an exemplary embodiment, there is a behind-the-ear (BTE) device, comprising an electronics component (e.g., the spine 330B, in that the spine 330B carries the electronics of the prosthesis, the sound processor sub-assembly 430, in that that contains electronics, etc.) and a power component (e.g., battery sub-assembly 452), removably attached to the electronics component. What has not yet been detailed is that in an exemplary embodiment, the BTE device is configured with electrical current protection at a plug-socket arrangement connecting the power component to the electronics component. In an exemplary embodiment, this is electrostatic discharge protection and/or signal path protection.

Briefly, in an exemplary embodiment, the BTE device is configured such that upon initial contact of the battery sub-assembly with the sound processor sub-assembly, prior to the battery sub-assembly being fully seated against the sound processor sub-assembly with respect to the longitudinal axis of the battery sub-assembly (e.g., before or after being canted about the longitudinal axis thereof to its final location), it is the negative contact 451 that first contacts the socket assembly, or at least it is the negative contact 451 that first contacts metallic components of the socket assembly, or at least it is the negative contact 451 that represents first contact between respective to metallic components of the battery sub-assembly and the sound processor sub-assembly, or at least it is the negative contact 451 that represents first contact between respective to metallic components of the battery sub-assembly and the sound processor sub-assembly, one or both of which are components that are in electrical communication with sensitive components of the battery and/or sound processor (as opposed to other components that are metallic, such as the male bayonet component 455, which, as detailed above, can be made out of titanium, and can be plated or coated with nickel, but which, as will be described in greater detail below, is electrically isolated from other components of the battery sub-assembly 452 in the case where the chassis 459 is plastic).

Figure 13:
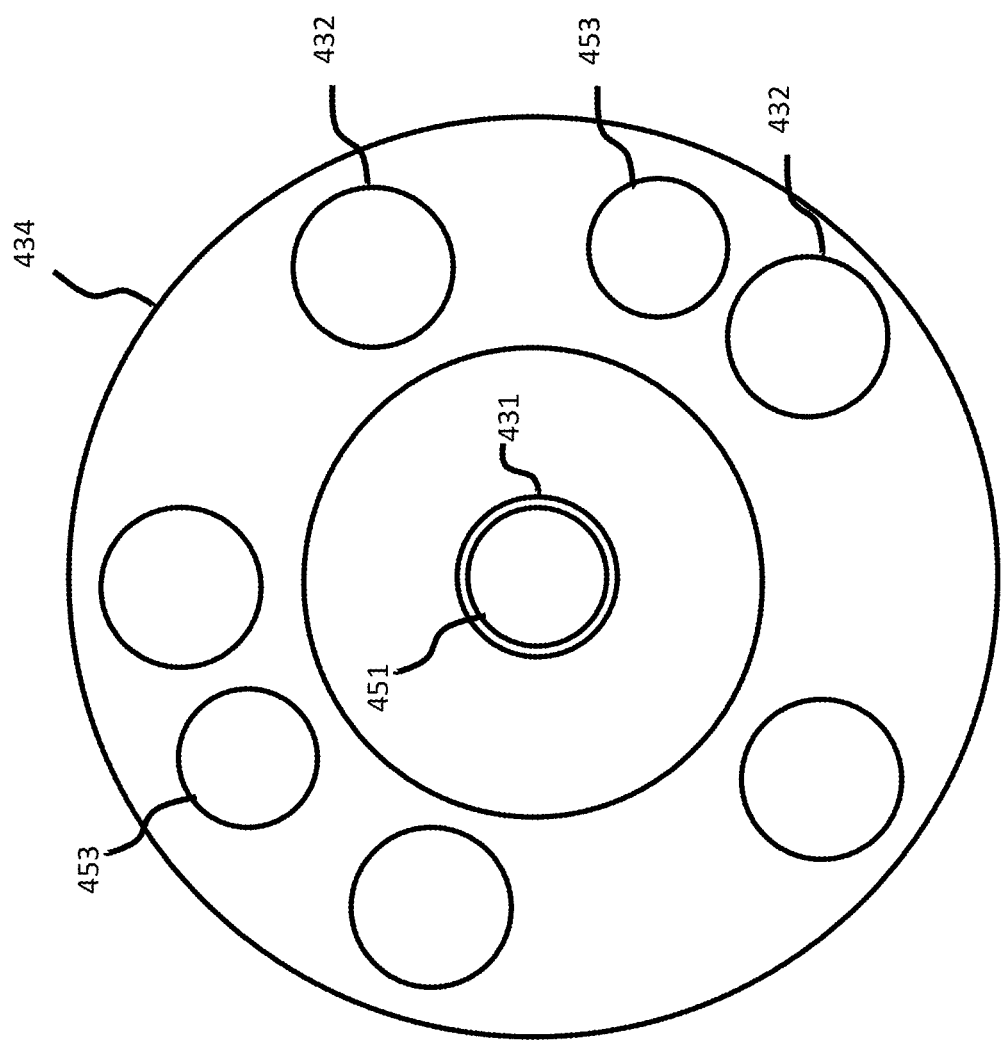
FIGS. 13-14 conceptually represent pin contact according to an exemplary embodiment.

In an exemplary embodiment, consistent with the embodiment of FIG. 10, the contacts 431 and 432 are arrayed as shown. The contacts 432 are arrayed in a manner such that when the battery sub-assembly is fully seated against the sound processor sub-assembly but prior to rotation of the battery sub-assembly about the longitudinal axis thereof to fully couple the battery sub-assembly to the sound processor sub-assembly, the contacts 453 are misaligned with the contacts 432. By way of example only and not by way of limitation, the tips of the contacts 453 come into contact with the plastic component 434 instead of the contacts 432, and thus there is no metal to metal contact between the contacts. However, contact 451 comes into contact with contact 431. FIG. 13 depicts a conceptual view of the various contacts superimposed upon one another in a view looking down the longitudinal axis of the battery sub-assembly 452, where the battery sub-assembly is fully seated against the sound processor sub-assembly, but is still canted relative to the sound processor sub-assembly (e.g., at the angle of FIG. 5 relative to the sound processor sub-assembly 430). As can be seen, contacts 453 are located adjacent contacts 432, representing lack of electrical contact between the two components, and instead representing contact with plastic piece 434 with respect to contact 453, where contacts 432 are electrically isolated from one another and thus contacts 453 via the plastic component 434. Conversely, contact 451 is coaxial with contact 431, representing contact with contact 451 and contact 431.

Figure 14:
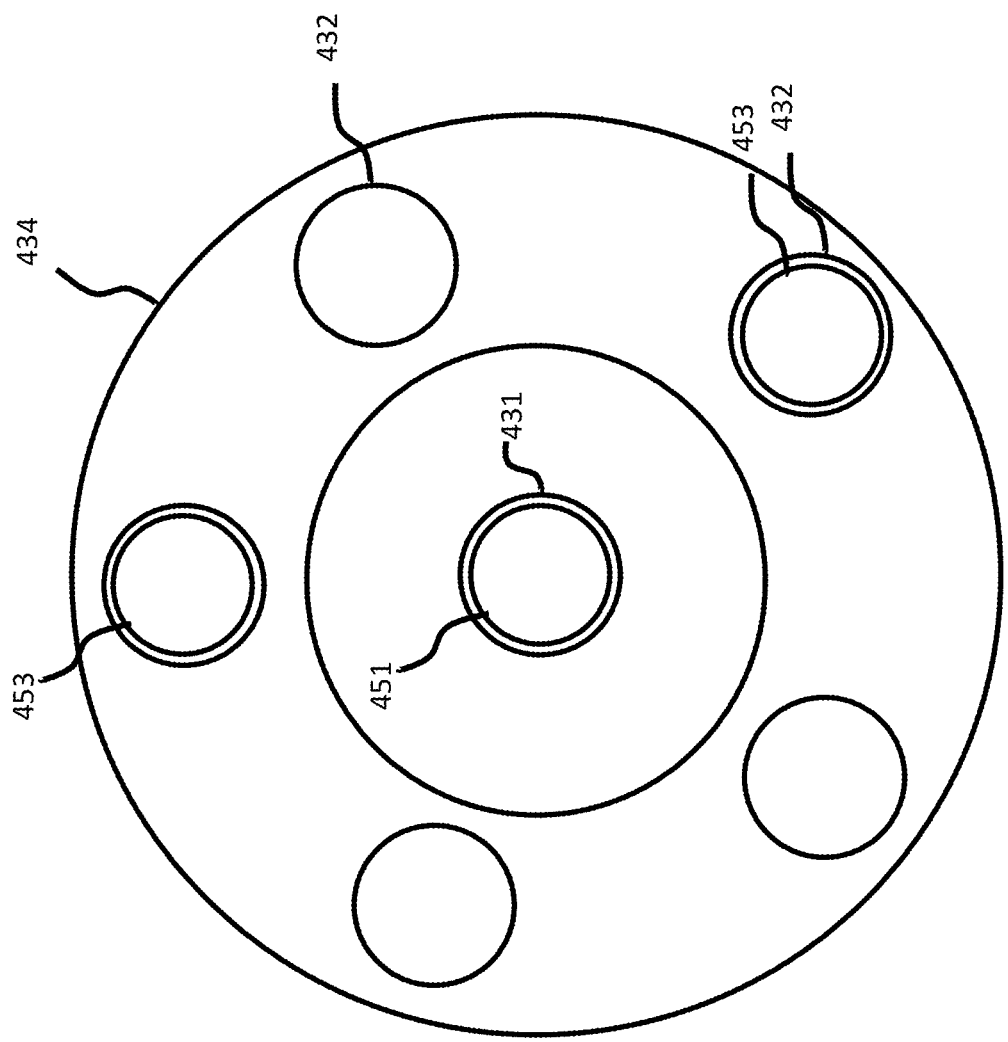

FIG. 14 depicts the relative locations of the contacts after the battery sub-assembly 452 is rotated so that it is fully connected to the sound processor sub-assembly 430. As can be seen, contact 453 is coaxial with contacts 432, thus establishing electrical communication between the respective contacts. While the embodiment of FIG. 14 depicts the contacts 453 being coaxial with contact 432, in some other embodiments, upon full coupling of the components, contacts 453 may not necessarily be coaxial with contact 432. All that is required for utilitarian value is that there be electrical communication between the respective contacts. Moreover, in at least some exemplary embodiments, only one of the contacts 453 will be in contact with one of the contacts 432. Any arrangement that can have utilitarian value with respect to some exemplary embodiments can be utilized in at least some exemplary embodiments.

Accordingly, in an exemplary embodiment, the aforementioned power component includes a positive terminal and a negative terminal of a battery (e.g., contacts 453 and 451, respectively), and the electronics component includes a first contact and a second contact electrically isolated from the first contact (e.g., any of contacts 432 and contact 431, respectively). In this exemplary embodiment, the first contact (432) is configured to be in electrical contact with the positive terminal (453) and the second contact (431) is configured to be in electrical contact with the negative terminal (451) when the power component is fully attached to the electronics component. Still further, in this exemplary embodiment, the BTE device is configured such that the negative terminal comes into electrical contact with the second contact before the positive terminal comes into contact with the first contact when the power component is initially attached to the electronics component. Indeed, in a specific embodiment of this embodiment, the positive terminal does not come into contact with the first contact until after the battery sub-assembly is rotated relative to the sound processor sub-assembly so as to fully couple the two components together.

In an exemplary embodiment of the just described embodiment, at least one of the negative terminal or the second contact is biased (e.g., spring biased) in a longitudinal direction of the respective BTE component so as to provide give in the longitudinal direction of the power component when the components are attached to one another to enable the first contact to come into electrical contact with the positive terminal. In this regard, as seen above, unless the contact 451 is enabled to retract into the plug assembly or otherwise move from its extended state, the battery sub-assembly will not be able to be fully seated against the sound processor sub-assembly, and thus will not be permitted to be rotated relative to the sound processor sub-assembly to bring the positive contacts 453 into contact with the contacts 432. That said, in some alternate embodiments, such as where the negative contact 451 is proud of the positive contacts 453, the plug assembly can be configured such that even if the contacts 432 are aligned with the contacts 453 with respect to the longitudinal axis upon the initial meeting of the battery sub-assembly with the sound processor sub-assembly, because the negative contact 451 is proud of the other contacts of the battery sub-assembly, the negative contact 451 will be the first contact that contacts the contacts of the sound processor sub-assembly. In an alternative embodiment, this arrangement can be present with respect to the contact 431 (e.g., as the biased movable contact), which can be proud relative to the contacts 432. In an alternate embodiment, this arrangement can be present with respect to both contacts 431 and 451. It is also noted that in an exemplary embodiment, the negative contact 451 is the last contact that remains in contact with the sound processor subassembly. That is, in an exemplary embodiment, the aforementioned above "firsts" are also the "lasts" when the battery subassembly is removed from the sound processor subassembly (by reversing the movements of FIGS. 5, 6, and 7).

Still further, as will be understood, in an exemplary embodiment at least one of the negative terminal or the second contact is biased in a lateral direction of the respective BTE component so as to provide give in the lateral direction when the components are attached to one another to enable the first contact to come into electrical contact with the positive terminal (by permitting the subsequent required rotation or by permitting the contacts to be moved to each other in the longitudinal direction irrespective of the subsequent rotation, etc.).

The above embodiments can have utilitarian value with respect to providing a ground from the battery sub-assembly to the sound processor component sub-assembly. Accordingly, in an exemplary embodiment, the battery sub-assembly is configured to provide power to the sound processor sub-assembly when removably attached thereto, and the BTE device is configured to provide a ground from the battery component to the sound processor sub-assembly. In an exemplary embodiment, this can protect the circuits of the electronics component in general, and the sound processor components in particular, and/or can protect a programming interface that connects to the electronics component/sound processor subassembly. With respect to the latter, the programming interface, in some embodiments, there are wired and/or wireless pods that are configured to be connected to the sound processor subassembly/electronics subassembly. In at least some exemplary embodiments of use, these pods are normally powered up and otherwise energized before they are connected to the sound processor subassembly. That is, the power and signals are already present on the connect pins on the connector thereof. On connection to these pods, there is utilitarian value with respect to the ground pin being made to make first contact before the power or signals are connected to the sound processor subassembly. This can have utilitarian value with respect to improving the likelihood that there is a proper return path. Conversely, if the power or signals are connected to the sound processor before the ground, the power may not necessarily have the correct return path and the signals may not necessarily have the right reference. In such an exemplary scenario, the system could potentially go into an undefined state.

Corollary to the above is that the power and/or signals should be disconnected first when the battery and/or programming interface is disconnected from the sound processor subassembly. This can have utilitarian value with respect to improving the likelihood that there will be safe operation of the system during disconnection and shutdown.

In any event, there is utilitarian value with respect to having a BTE device that is arranged such that the negative terminal of the battery subassembly and the corresponding contact of the sound processor subassembly are the first and last electrical components to contact each other with respect to attachment and removal of the battery or any other component, respectively.

In at least some exemplary embodiments, this can provide a safeguard against stray signals, as noted above, or otherwise prevent a scenario where a positive signal is provided to the wrong contact. In at least some embodiments, there is utilitarian value with respect to preventing or otherwise reducing the likelihood that the positive terminal(s) of the battery will contact the wrong contact(s) of the sound processor subassembly. Moreover, the teachings detailed herein can be utilized in some exemplary embodiments to ensure otherwise increase the possibility that a contact of the sound processor subassembly that is to touch the negative terminal of the battery during normal operation does not touch a positive terminal of the battery, and vice versa. Such is also the case with respect to the aforementioned pods.

Accordingly, the above-noted pin/contact arrangement provides signal path protection as the electrical current protection of the BTE device at the plug-socket arrangement connecting the power component of the electronics device to the electronics component. For example, in at least some exemplary embodiments, a signal intended for a negative contact cannot be, or at least is less likely to be, provided to a positive contact, and/or a signal intended for a positive contact cannot be, or at least is less likely to be, provided to a negative contact. In any event, in at least some exemplary embodiments, the signal path protection is achieved by ensuring that the ground connection makes first contact on connection and breaks last on disconnection. This can be because there is always a path to the ground while any other signals are present.

It is also noted that in at least some exemplary embodiments, the above-noted pin/contact arrangement can have utilitarian value with respect to providing electrostatic discharge protection between the sound processor sub-assembly and the battery sub-assembly in that, by way of example only and not by way of limitation, the first metallic component of the sound processor sub-assembly that comes into contact with a metallic component of the battery subassembly component comes into contact with the negative terminal of the battery sub-assembly, and thus a path to ground is provided so that any electrostatic discharge is mitigated owing to the ground to the battery sub-assembly that is first established before any other pathway for electrostatic discharge can be established. This can be achieved by any of the aforementioned arrangements (e.g., where the negative terminal 451 of the battery is the first component to contact the socket assembly, etc.).

In an exemplary embodiment, there is BTE device that is configured to frustrate electrostatic discharge to active electrical contact(s) of the electronics component from the battery sub-assembly and encourage electrostatic discharge to passive electrical contact(s) of the sound processor subassembly from the battery sub-assembly to the extent that electrostatic discharge will occur when the battery subassembly is connected to the sound processor sub-assembly.

As noted above, in some embodiments, the socket 830 includes a chassis 437 that is a titanium-based component and/or a component that is plated or otherwise coated with nickel or some other metallic component. Accordingly, in an exemplary embodiment, the electronic component includes a socket having an electrically conductive body. Still further, as noted above, in some embodiments, the male portion of the bayonet coupling of the plug 952 is also made out of titanium and/or is a component that is plated or otherwise coated with nickel or some other metallic component. Accordingly, in an exemplary embodiment, the power component includes a plug having an electrically conductive body, the plug having a basin (basin 458) in which electrical contacts are present (contacts 453, for example). An electrostatic discharge limiting component is located between at least one of the electrically conductive body of the power component or the electrically conductive body of the socket and the electrical contacts when the power component is at least initially connected to the electronics component. In this regard, the electrostatic discharge limiting component is the rib 457 that is located between the body 455 and the contacts 453. That said, in an alternate embodiment, the rib 457 can be located on the socket assembly 830, which rib can extend outwards so as to come in between the male component of the bayonet coupling (body 455) and the contacts 453 when the battery sub-assembly is moved towards the sound processor sub-assembly. Any arrangement that can be an electrostatic discharge limiting component (which includes an electrostatic discharge preventing component) can be utilized in at least some exemplary embodiments.

The rib 457 frustrates electrostatic discharge between the titanium male bayonet coupling component 455 and one or more of the contacts 451 and/or 453 (briefly, the rib 454 can also frustrate electrostatic discharge between the coupling component 455 and the contact 451, in at least some exemplary embodiments, depending on the dimensioning of the rib 454). In an exemplary scenario, such as in a low humidity environment, a child or the like can be wearing the BTE device, and a caregiver, such as a parent, could walk across a carpet and touch the BTE device before touching anything else. This could transfer electrons from the caregiver to the BTE device. Depending on various conditions, in some exemplary scenarios, the electrons can ultimately reach the bayonet coupling 455. Because the rib 457 is interposed between the metallic male bayonet coupling 455 and the contacts of the battery sub-assembly, any electrons that reach the male bayonet coupling 455 will be frustrated from reaching the contacts.

In an exemplary embodiment, the BTE device is such that the electronics component includes a socket having an electrically conductive body, the power component includes a plug having an electrically conductive body, the plug having a basin in which electrical contacts are present, and electrostatic discharge shield is located between the electrically conductive body of the power component and the electrical contacts, and the electrically conductive body is configured to provide mechanical releasable coupling of the power component to the electronics component.

Some embodiments include an environmental barrier at the interface between the sound processor sub-assembly and the battery sub-assembly. By way of example only and not by way of limitation, as noted above, seal 433 is located on the socket assembly, which seal can be a Viton seal, such as a Viton® A401C (shore A hardness 70+/−5). This can be in the form of a gasket on the socket assembly, but can also or instead be located on the plug assembly. In some embodiments, any fluoroelastomer can be used as the material of the seal. Also, in some embodiments, there is a rib 454 that also provides an environmental barrier, as will be described below.

In view of the above, it can be seen that an exemplary embodiment includes a behind-the-ear (BTE) device, comprising an electronics component (e.g., sound processor sub-assembly 430); and a power component (e.g., battery sub assembly 452), removably attached to the electronics component. The BTE device is configured with an environmental barrier at the general interface between the electronics component and the power component. By "general interface," it is meant the general area where the two components interface with each other, and this does not necessarily require that the environmental barrier be a barrier that contacts both components, as will be described below.

In an exemplary embodiment, the environmental barrier is a moisture barrier. With respect to the seal/gasket 433, it is to be understood that this seal 433 can provide a gas barrier and/or a liquid barrier from the ambient environment to the location inboard of the seal 433. In an exemplary embodiment, the seal 433 is a flexible seal that compresses against the top surface of the male portion of the bayonet coupling 455 and/or the top surface of the rib 457. This is depicted in FIG. 12, where the seal 433 is presented in its non-compressed state so as to show that there would be interference between the respective components in the absence of the flexibility of the seal. As can be seen, the seal 433, in conjunction with the plastic component 434 establishes an environmental barrier from the ambient environment and the area inside the basin 458 that is established by the chassis 459 and/or via the male portion of the bayonet coupling 455. Accordingly, in this exemplary embodiment, such prevents moisture such as in the form of humid air and/or in the form of liquid from traveling from the external environment into the basin 458, and thus potentially coming into contact with the contacts 451, 453, 432 and/or 431, which could cause corrosion or otherwise could cause a short circuit, or some other bad phenomenon.

Accordingly, in view of the above, in an exemplary embodiment, there is a BTE device, wherein the electronics component includes a socket and the power component includes a plug, the plug having a basin in which electrical contacts are present, and a moisture-resistant (which includes moisture proof) seal is located between a surface of the socket and a surface of the plug, the water-resistant seal being configured to provide a seal about the basin when the power component is attached to the electronics component.

Briefly, with reference to FIG. 12, it can be seen that the seal has a double bead, where a first bead comes into contact with the male component of the bayonet coupling 455, and a second bead comes into contact with the plastic rib 457, thus forming a double seal. In some embodiments, three or more beads are utilized. Conversely, in some embodiments, only one bead is utilized. Indeed, in some embodiments, the seal is simply an O-ring or the like having a circular cross-section, a rectangular cross-section, etc. any arrangement of a seal that can have utilitarian value can be utilized in at least some exemplary embodiments.

Consistent with the teachings detailed above, the electronics component 440 includes a socket, such a socket assembly 830, and the power component 452 includes a plug such as plug assembly 952, wherein the plug includes a basin (458) in which electrical contacts are present (contacts 453, for example). In this exemplary embodiment, the BTE device is configured to frustrate water intrusion into the basin when the power component is fully removably attached to the electronics component. In an exemplary embodiment, the frustration of water intrusion is the full prevention of water intrusion when the water is not under pressure. In an exemplary embodiment, the frustration of water intrusion is the limiting of water intrusion when the water is not under pressure relative to that which would otherwise be the case in the absence of the aforementioned environmental barrier. In an exemplary embodiment, for a given period of time, such as a statistically significant period of time, the amount of water that enters is less than 90, 80, 75, 70, 65, 60, 55, 50, 45, 40, 35, 30, 25, 20, 15, 14, 13, 12, 11, 10, 9, 8, 7, 6, 5, 4, 3, 2, 1, 0.5, 0.25 percent or less relative to that which would otherwise be the case, all other things being equal. In an exemplary embodiment, the frustration of water intrusion is the full prevention of water intrusion when the water is under a pressure difference between the basin 458 and the ambient environment having a ratio, where the environmental pressure is in the denominator, of 1.01, 1.02, 1.03, 1.04, 1.05, 1.06, 1.07, 1.08, 1.09, 1.1, 1.15, 1.2, 1.25, 1.3, 1.35, 1.4, 1.45, 1.5, 1.6, 1.7 or more, or any value or range of values therebetween in 0.001 increments (e.g., 1.032, 1.111, 1.000 to about 1.555, etc.). It is also noted that in an exemplary embodiment, with respect to the aforementioned pressures, the frustration of water intrusion is the partial prevention of water intrusion, where the partial prevention is such that for a given period of time, such as a statistically significant period of time, all other things being equal, the amount of water that enters the basin 458 from the ambient environment is less than 90, 80, 75, 70, 65, 60, 55, 50, 45, 40, 35, 30, 25, 20, 15, 14, 13, 12, 11, 10, 9, 8, 7, 6, 5, 4, 3, 2, 1, 0.5, 0.25 percent, or less of that which would otherwise be the case.

It is also noted that in at least some exemplary embodiments, the aforementioned water frustration is also applicable to gas frustration (e.g., humid air).

As noted above, in at least some embodiments, the electronics component 440 and the power component 452 are configured to rotate relative to one another to removably connect the power component to the electronics component. In this regard, the plug slides along a surface of the moisture-resistant seal during the rotation. Here, there is utilitarian value to having a material of the seal have a relatively high wear resistance and there is utilitarian value to having a seal that does not stick to the plug when exposed to certain temperatures, such as (60 degree Celsius for more than 12, 18 or 24 hours, etc.). In an exemplary embodiment, there is utilitarian value with respect to having a seal that has a low friction coefficient relative to the component to which it contacts to establish the seal.

While the embodiments above have focused on the seal located on the socket assembly (but could also or instead be located on the plug assembly), that provides a moisture barrier between the ambient environment and the basin of the plug assembly, some alternate embodiments of an environmental barrier utilize a berm type arrangement or a dam type arrangement instead of or in addition to the utilization of the above-noted seal. More specifically, as described above, some exemplary embodiments include rib 454 that extends completely about negative contact 451 of the battery sub-assembly. In an exemplary embodiment, rib 454 extends in a concentric manner about contact 451. That said, in an alternate embodiment, such is not the case. Still further, while the embodiment depicted in FIG. 11 depicts a rib 454 that is somewhat offset from the outer diameter of the contact 451, in some alternate embodiments, the rib 454 can instead be a mound of the like. Some additional details of this will be described in greater detail below. In any event, in view of this, it is to be understood that in an exemplary embodiment, the BTE device is such that the electronics component can include a socket having a basin and an electrical contact therein, and the socket incudes an elevated portion elevated from a floor of the basin, the electrical contact being in the elevated portion. In an exemplary embodiment, this elevated portion is the rib 454.

Figure 15:
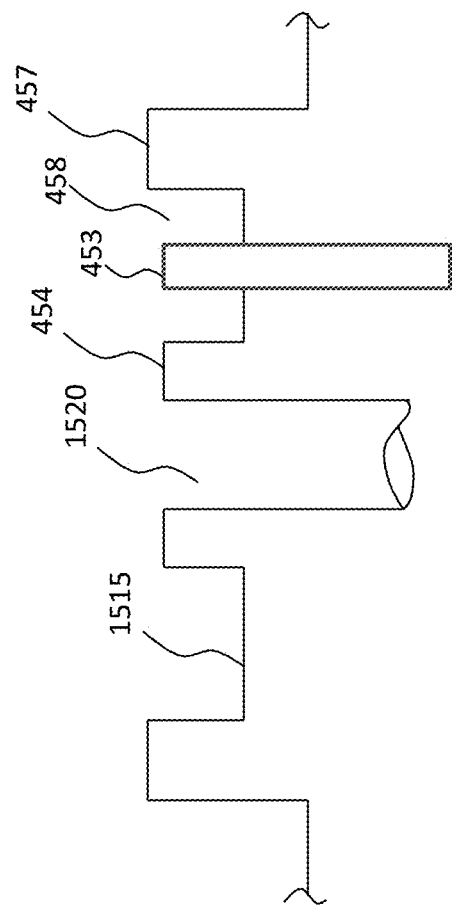
FIGS. 15-21 variously represent disclosure associated with some of the components of the battery subassembly located within the confines of the male bayonet component of the battery subassembly.

The rib 454 has utilitarian value in that the rib 454 forms a barrier, by way of analogy, to a flood wall, about the contact 451 that prevents liquid, at least in limited amounts, that may be present in the basin 458, from reaching contact 451. More specifically, FIG. 15 presents a quasi-cross-sectional view of the chassis 459 centered about the hole 1520 for the contact 451 (the contact 451 is not shown). As can be seen, the rib 454 and the rib 457 correspond to that of the above figures. Contact 453 is located in the basin 458, and extends through the floor 1515 of the basin 458. It is briefly noted that back lines are not shown in FIG. 15 for purposes of clarity.

Figure 16:
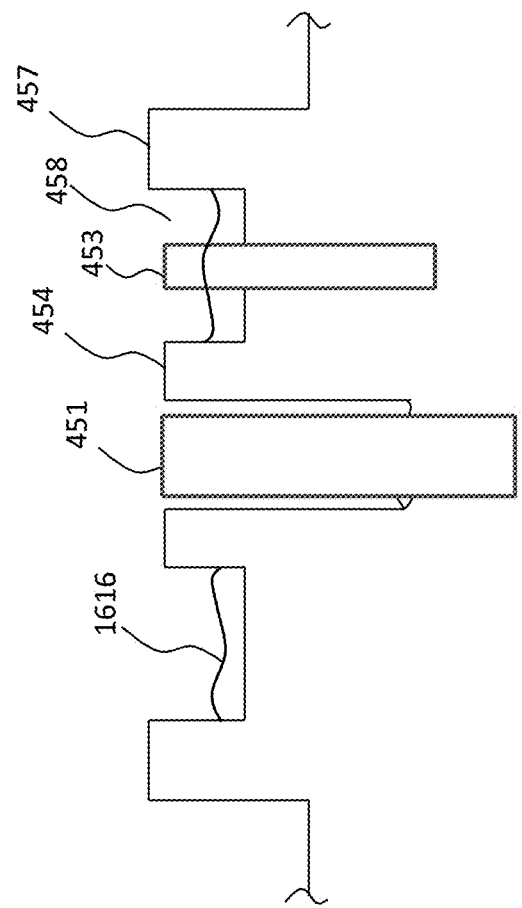

FIG. 16 depicts an exemplary scenario where a liquid 1616 has entered the basin 458, and owing to gravity, is located proximate the floor of the basin. Because the sound processor is worn on the head such that the battery subcomponent is below the sound processor subcomponent, the liquid 1616 will pull at the floor the basin 458 as opposed to pulling at the top of the basin. As can be seen, the flood barrier 454/liquid barrier 454 prevents the liquid 1616 from entering into the hole 1520 and otherwise reaching the contact 451. Accordingly, this liquid 1616, which could be a salt containing liquid such as sweat or the like, cannot establish a conductive path between the positive terminals 453 and the negative terminal 451 owing to the rib 454/flood barrier 454. This is as opposed to an alternate embodiment, depicted in FIG. 17, where there is no flood barrier 454, where liquid 1616 extends from contact 4532 contact 451. As can be seen, such modes of the occurrence of this phenomenon may not necessarily "fill" the bottom of the basin 458. It is possible that liquid 1616 can slosh around or the like or otherwise be a bead of a liquid located on the floor 1515 of the basin 458, which bead can have a diameter that extends from the contact 4512 contact 453.

Figure 17:
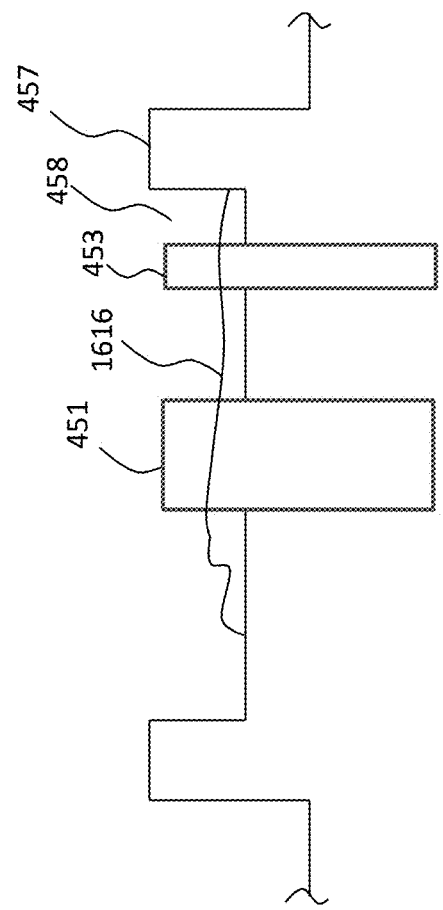
Figure 18:
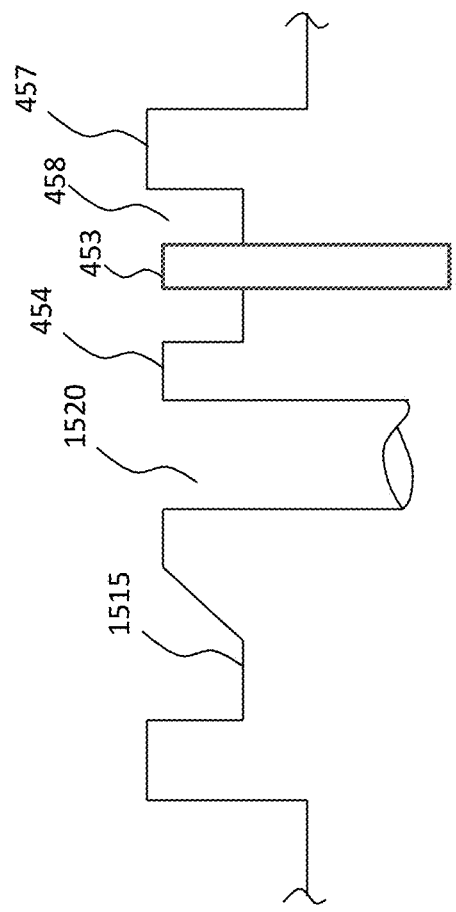
Figure 19:
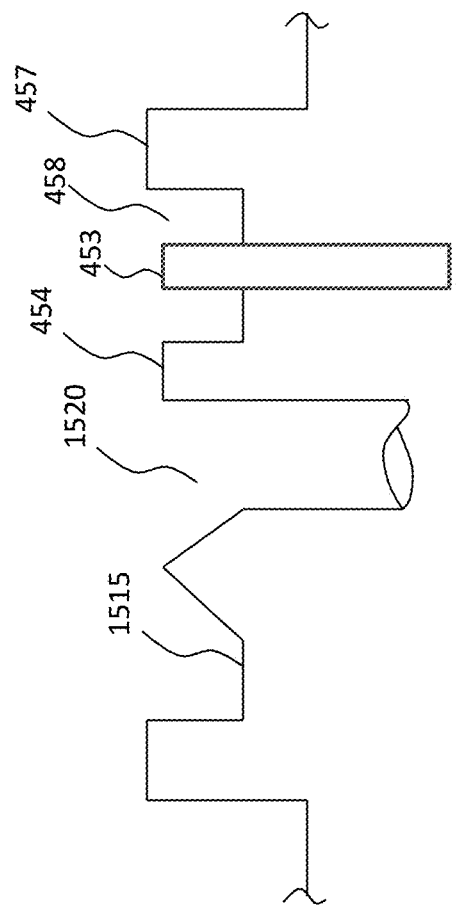

In at least some exemplary embodiments, FIG. 17 represents a failure mode because the presence of the salt containing fluid 1616 and its contact with the positive and negative terminals of the battery can cause corrosion. Conversely, with the barrier 454 in place, the contact of the fluid between both positive and negative terminals is less likely to occur (including will not occur). It is noted that while the embodiments depicted herein to the flood barrier around the negative terminal 451, in some alternative embodiments, the flood barrier can be presented around the positive terminal(s). Any arrangement that can prevent a fluid or otherwise reduce the possibility of a fluid from coming into contact with both the positive terminal and the negative terminal and/or any arrangement that can reduce the amount of fluid that comes into contact with both the positive terminal and the negative terminal can have utilitarian value and otherwise can be utilized in at least some exemplary embodiments. In this regard, while a rib having a wall having a rectangular cross-section has been utilized in the above embodiments, in some alternate embodiments, the barrier 454 can have a different configuration, such as that seen in FIG. 18 in FIG. 19. Also as can be seen from these figures, the barrier 454 can be of a different configuration with respect to radial location about the contact 451. That said, as seen above, the barrier can have a common/standard cross-section with respect to radial location about the contact 451.

Figure 20:
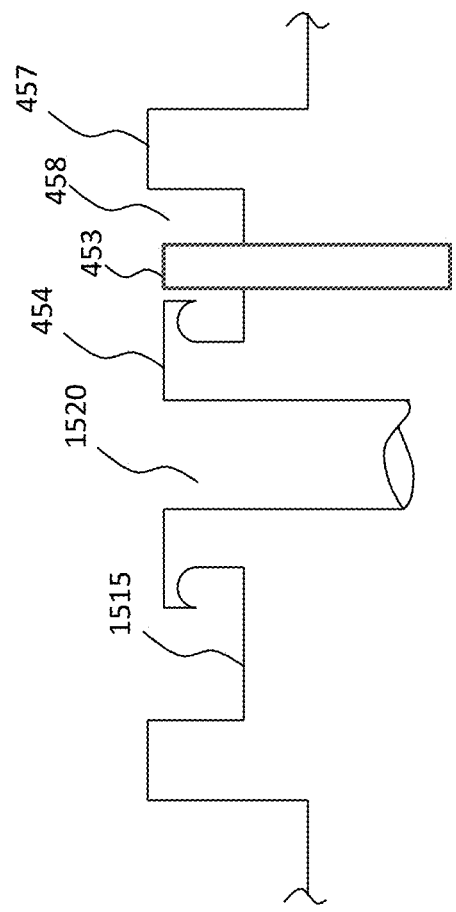

FIG. 20 depicts an alternate embodiment of a barrier 454, which includes a splash guard feature with respect to the barrier 454 where the liquid, if present in the basin 458, and if sloshing around on the floor thereof, comes into contact with the outside wall of the barrier 454, and thus might be directed up words towards the curved portion which then directs the liquid downward.

Figure 21:
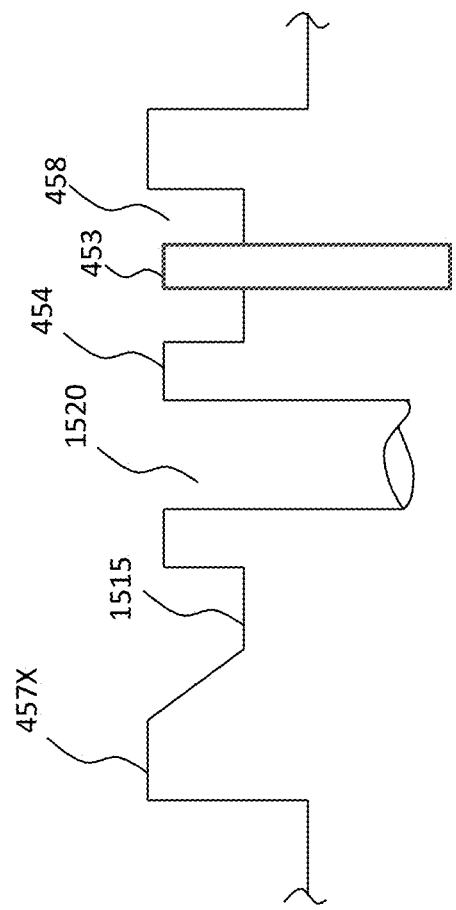

While the above is focused on the rib 454 and some of the exemplary various geometries thereof, it is noted that the rib 457 can also have different geometries, such as that seen in FIG. 21, with respect to rib 457X, and also that the rib 457 can have a different configuration with respect to radial location about the basin 458. It is noted that any of a variety of barriers can be implemented in accordance with many embodiments of the invention. Any barrier or body that can enable the teachings detailed herein can be used in some embodiments.

In view of the above, it can be seen that the rib 457, the basin 458, and the rib 454 have a quasi-crater like relationship with each other. In view of the above, in Moon crater terms for example, it can be seen that in an exemplary embodiment, the power component includes a planar body (e.g., the portion of the chassis beneath the male bayonet connector portion) from which a crater-like component rises (e.g., the portion inboard of the male bayonet connector portion, the crater-like component including a crater wall (e.g., rib 457) and a central peak (e.g., the ribs 454) in which a first electrical contact 451 is located. Further, a second contact (e.g., one or more of context 453) electrically isolated from the first contact with respect to a plane normal to the longitudinal extension of the second electrical contact is located between the crater wall and the central peak, the second contact being of an opposite polarity than the first contact.

By "electrically isolated from the first contact with respect to a plane normal to the longitudinal extension of the second electrical to contact," it is meant that the material between the two electrical contacts is nonconductive. Of course, because the positive and negative terminals are part of the battery, the contacts are ultimately in electrical conductivity with one another. Another way of saying this is that the components of the battery sub-assembly (and/or the sound processor sub-assembly) that support the contacts are electrically nonconductive, or otherwise other than the circuit of which the contacts are a part, the contacts are electrically isolated from one another.

Still further, in view of the above, it can be seen that in an exemplary embodiment, the power component includes a planar body from which a plug rises, the plug being formed by a first circular rib, the first circular rib encompassing a first electrical contact and a second electrical contact electrically isolated from the first electrical contact other than the contact being a part of the same circuit and being of a different polarity than the first electrical contact. A second circular rib encompasses the first electrical contact and forms, at least with the aid of gravity, a liquid barrier between the first electrical contact and the second electrical contact. In this regard, in at least some exemplary embodiments, the barrier would not be a barrier without the presence of gravity, just as a glass will not hold a liquid in a utilitarian manner without the presence of gravity. Corollary to this is that in at least some exemplary embodiments, there is no seal between the top of the ribs 454 and the socket assembly when the battery sub-assembly and the sound processor sub-assembly are fully connected to one another. That is, in an exemplary embodiment, in the absence of gravity, liquid could travel from the basin, up over the ribs 454, and into the hole 1515 or otherwise to the contact 451. Still, owing to the viscous nature of the liquids/surface tensions that would be present in any likely scenario of liquid intrusion into the basin (e.g., sweat, low pressure water, etc.) and the relative dimensions of the rib 454 relative to the plastic component 434, little to no liquid will be able to travel from the basin to reach the contact 451. To the extent liquid does reach the contact 451, owing to the geometry of the BTE device when fully assembled (e.g., relative dimensions, etc.) in at least some exemplary embodiments, the liquid will not be a contiguous liquid with any liquid that contacts the other negative terminals. Accordingly, the liquid will not establish an electrically conductive path between the two terminals in at least some exemplary scenarios.

That said, in some alternate embodiments, a seal can be located on the plastic component 434 and/or on the top of the ribs 454 in a manner analogous to seal 433. Any arrangement that can prevent liquid from contacting the positive terminal and the negative terminal at the same time which liquid establishes a conductive path there between can be utilized in at least some exemplary embodiments. Still further, while the embodiments detailed above have focused on the barrier being a liquid barrier, in at least some exemplary embodiments, such as embodiments where there is a seal present between the ribs 454 and the plastic component 434, the ribs 454 can also be a gas barrier in that it prevents, for example, humid air from traveling from the basin 4582 the hole 1515.

Another way of describing some exemplary embodiments is that the power component includes a first electrical contact and a second electrical contact electrically isolated from the first electrical contact (as detailed herein, other than the fact that the contacts are part of the same circuit) and being of a different polarity than the first electrical contact. The power component includes a liquid barrier between the first electrical contact and the second electrical contact. Again, in some embodiments, the liquid barrier can also be a gas barrier. Implicit in this is that the barrier can be a multicomponent structure (e.g., the barrier can be the ribs plus a seal, whether the seal is permanently attached to the ribs for whether the seal is part of the socket assembly that comes into contact with the ribs 454.

Again, while the embodiments herein describe the wall surrounding the basin as ribs and the barrier is ribs, in other embodiments, other structure can be utilized.

Another aspect of the BTE device according to some embodiments is that the sound processor sub-assembly is configured for relative longevity in general, and in particular with respect to the deleterious effect that might be present upon repeated removal and attachment of battery subassemblies to the sound processor subassemblies. In this regard, in at least some exemplary scenarios of use, two or more batteries could be changed out from the same sound processor sub-assembly in a given day. By way of example only and not by way of limitation, a recipient that has battery A and battery B can start the day with battery A attached to the sound processor sub-assembly, drain battery A, remove battery B from the sound processor sub-assembly, attach fully charged battery B to the sound processor sub-assembly, drain battery B, remove battery B from the sound processor sub-assembly and then reattached now fully charged battery A to the sound processor sub-assembly. This can occur every day of the year for the life of the sound processor, which could be 3, 4, 5, 6, 7, 8, 9, 10, 11, 12, 13, 14, 15, 16, 17, 18, 19, or 20 years or more. The batteries are considered relatively disposable and otherwise a component that is relatively inexpensive relative to the sound processor sub-assembly, and because the sound processor sub-assembly is often fitted to the given recipient and otherwise contains programming unique to the recipient, there is utilitarian value with maintaining the sound processor sub-assembly as a usable component for as long as possible, certainly much longer than the utilitarian life of the batteries.

Every time that a battery is removed and installed from the sound processor sub-assembly, wear occurs with respect to the battery and the sound processor subassemblies. The teachings detailed herein enable the batteries to wear well before the sound processor assembly wears, and in fact, the teachings detailed herein enable the battery to not impart as much wear onto the sound processor (or more specifically, onto the female component of the bayonet coupling) as otherwise might be the case. In this regard, the teachings detailed herein make the battery sub-assembly, and more accurately, the male bayonet connector component a sacrificial component relative to the sound processor assembly.

It is further briefly noted that the bayonet coupling components have utilitarian value if they are strong and otherwise robust and otherwise wear resistant. In this regard, there is more utilitarian value with respect to utilizing metallic bayonet components in general, and titanium bayonet components in particular, as opposed to utilizing plastic bayonet components or polymer bayonet components, even if such is reinforced or otherwise harden. Some exemplary embodiments utilize a titanium coupling component for the sound processor sub-assembly and a plastic coupling component for the battery sub-assembly. Such is utilitarian value with respect to preventing or otherwise limiting wear on the components of the sound processor sub-assembly. However, in at least some embodiments, the plastic components of the battery sub-assembly can sometimes wear out earlier than the life of the battery. Accordingly, there is utilitarian value with respect to utilizing titanium components for the bayonet coupling on both the sound processor sub-assembly and the battery sub-assembly. Thus, in an exemplary embodiment, there is a behind-the-ear (BTE) device, comprising a sound processor sub-assembly and a battery sub-assembly, removably attached to the sound processor sub-assembly. In this exemplary embodiment, the BTE device is configured such that component(s) of the battery sub-assembly (e.g., the male bayonet coupling component 455, or an assembly of components in some other embodiments) that enable the removable attachment to the sound processor sub-assembly will wear out before component(s) of the sound processor sub-assembly (e.g., the female bayonet coupling component 435, or an assembly of components in some other embodiments) that enable removable attachment to the battery sub-assembly due to repeated removal and attachment of the battery sub-assembly from/to the sound processor sub-assembly.

In an exemplary embodiment, the BTE device is configured such that for a statistically constant number of battery removals and attachments, the sound processor sub-assembly is configured to enable continued attachment and detachment of a battery sub-assembly in a manner that permits utilitarian operation of the sound processor sub-assembly for a period of at least 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 9, 10, 11, 12, 13, 14, 15, 16, 17, 18, 19, or 20 or more times the utilitarian life of the battery with respect to either wear of the coupling components (i.e., the coupling components will permit utilitarian coupling to the sound processor sub-assembly to enable utilitarian operation thereof) or battery life (i.e., the period of time that the battery enable utilitarian charging and discharge of the battery).

In some exemplary embodiments, the aforementioned utilitarian features of the BTE device vis-à-vis longevity of the sound processor sub-assembly are achieved by providing surfaces of the component(s) of the sound processor sub-assembly that enable removable attachment to the battery sub-assembly are harder than interfacing surfaces of the component(s) of the battery sub-assembly that enable removable attachment to the sound processor sub-assembly. In an exemplary embodiment, the surfaces of the sound processor sub-assembly are at least 1.05, 1.1, 1.15, 1.2, 1.25, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.25, 3.5, 3.75, or 4 times harder than the corresponding surfaces of the battery sub-assembly.

In at least some exemplary embodiments, as noted above, the components of the coupling are made of titanium/titanium alloys. Still further, in some embodiments, the titanium is coated or otherwise a plated with another material. In an exemplary embodiment, the material is a nickel containing material. Accordingly, in an exemplary embodiment, surfaces of the component(s) of the sound processor sub-assembly that enable removable attachment to the battery sub-assembly that interface with surfaces of the component(s) of the battery sub-assembly that enable removable attachment to the sound processor sub-assembly are nickel containing surfaces. Also, in some embodiments, the surfaces are established via a nickel PTFE coating. Thus, in some exemplary embodiments, the surfaces of the component(s) of the sound processor sub-assembly that enable removable attachment to the battery sub-assembly that interface with surfaces of the component(s) of the battery sub-assembly that enable removable attachment to the sound processor sub-assembly are made up of nickel PTFE coated titanium/plated titanium. In an exemplary embodiment, the coating on a titanium socket is 8-12 micron plating of Ni PTFE coating (with heat treatment to HV500-550 hardness) and the coating on titanium plug is 8-12 micron plating of Ni PTFE coating (without heat treatment to HV300-350 hardness). Any hardness that can enable the teachings detailed herein can be used in some embodiments.

In an exemplary embodiment, the above-noted hardnesses are achieved by heat treating the pertinent components of the bayonet connector of the sound processor subcomponent and not heat treating the pertinent components of the battery subcomponent. That is, in some embodiments, components of the bayonet coupling of the battery sub-assembly are not heat-treated components. That said, in an alternate embodiment, this can be achieved by heat treating the pertinent components of the bayonet connector of the sound processor subcomponent to a hardness that is harder than that which resulted from the treatment of the pertinent components of the bayonet connector of the battery subcomponent. Thus, in an exemplary embodiment, the component(s) of the sound processor sub-assembly that enable(s) removable attachment to the battery sub-assembly that interface with surfaces of the component(s) of the battery sub-assembly that enable removable attachment to the sound processor sub-assembly are heat treated to a first hardness and the component(s) of the battery sub-assembly that enable(s) removable attachment to/from the sound processor sub-assembly that interface with surfaces of the component(s) of the sound processor sub-assembly that enable removable attachment to/from the battery sub-assembly are non-heat treated components and have a second hardness less than the first hardness. This second hardness can be achieved via heat treatment or via-not heat treating the pertinent components.

As noted above, plug assembly of the battery sub-assembly of the BTE device can be made of a plastic chassis 459 and a titanium male bayonet coupling 455. The male bayonet coupling 455 has the aforementioned features detailed above, at least in some embodiments, these are the hardness, plating/coating, etc. According to some exemplary embodiments, the chassis 459 is injection molded about the male bayonet coupling 455. More specifically, in an exemplary embodiment, the titanium body male bayonet coupling 455 is fabricated, and then it is plated/coated with nickel PTFE, and, in some embodiments but not others, heat treated. The resulting male bayonet coupling 455 with the nickel PTFE is then placed in a mold, or at least a portion thereof is placed enabled, and plastic is injected into the mold so that the plastic is molded about the bottom portion of the male bayonet coupling 455. In this regard, referring to FIG. 12, it can be seen that the male bayonet coupling 455 has a first portion that is proud of the top surface of the chassis 459 (i.e., the surface facing the sound processor sub-assembly in the embodiment of FIG. 12) and a second portion monolithic with the first portion that is embedded in the chassis 459 (although the components can be separate components attached to one another (e.g., interference fitted together, etc.). According to an exemplary embodiment, this enables the male bayonet coupling 455 to be electrically isolated from all the other metallic components of the plug assembly, as well as all the other metallic components of the battery sub-assembly, while still achieving the structural features of a titanium bayonet coupling. The plastic chassis 459 covers almost all of the opening of the housing of the battery sub-assembly, and thus, with the housing and the other components, creates a complete electrical insulation assembly about the electrically conductive and reactive components of the battery sub-assembly save for the battery terminals, even though the conductive component of the male portion of the bayonet coupling extends into the battery sub-assembly.

Thus, in an exemplary embodiment, there is a BTE device including a sound processor sub-assembly and a battery sub-assembly, wherein at least a portion of the component(s) of the battery sub-assembly that enable removable attachment to the sound processor sub-assembly (e.g., the male portion of the bayonet coupling 455) are imbedded in an injection molded plastic body of the battery sub-assembly (e.g., the chassis 459).

It is briefly noted that while the embodiments detailed above have focused on the battery sub-assembly as including the male components of the bayonet coupling, and the sound processor sub-assembly as including the female components of the bayonet coupling, in some alternative embodiments, this is reversed. Indeed, any feature disclosed herein regarding the plug assembly associated with the battery sub-assembly can be present in the sound processor sub-assembly, and any feature disclosed herein regarding the socket assembly associated with the sound processor sub-assembly can be present in the battery sub-assembly. Any arrangement that can enable the teachings detailed herein to be practiced can be utilized in at least some embodiments.

In an exemplary embodiment, there is also a method of utilizing a BTE device in general, and a sound processor sub-assembly in particular, where the method includes utilizing the sound processor sub-assembly for at least 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 9, 10, 11, 12, 13, 14, 15, 16, 17, 18, 19, or 20 or more times the utilitarian life of the battery with respect to either wear of the coupling components or battery cell failure. In an exemplary embodiment, the utilitarian life of the battery sub-assembly when used once per day for a full discharge cycle is 1, 1.25, 1.5, 1.75, 2, 2.25, 2.5, 2.75, 3, 3.25, 3.5, 3.75, 4, 4.25, 4.5, 4.75, or 5 years, and thus the method can also include using a battery sub-assembly for those periods.

Figure 22:
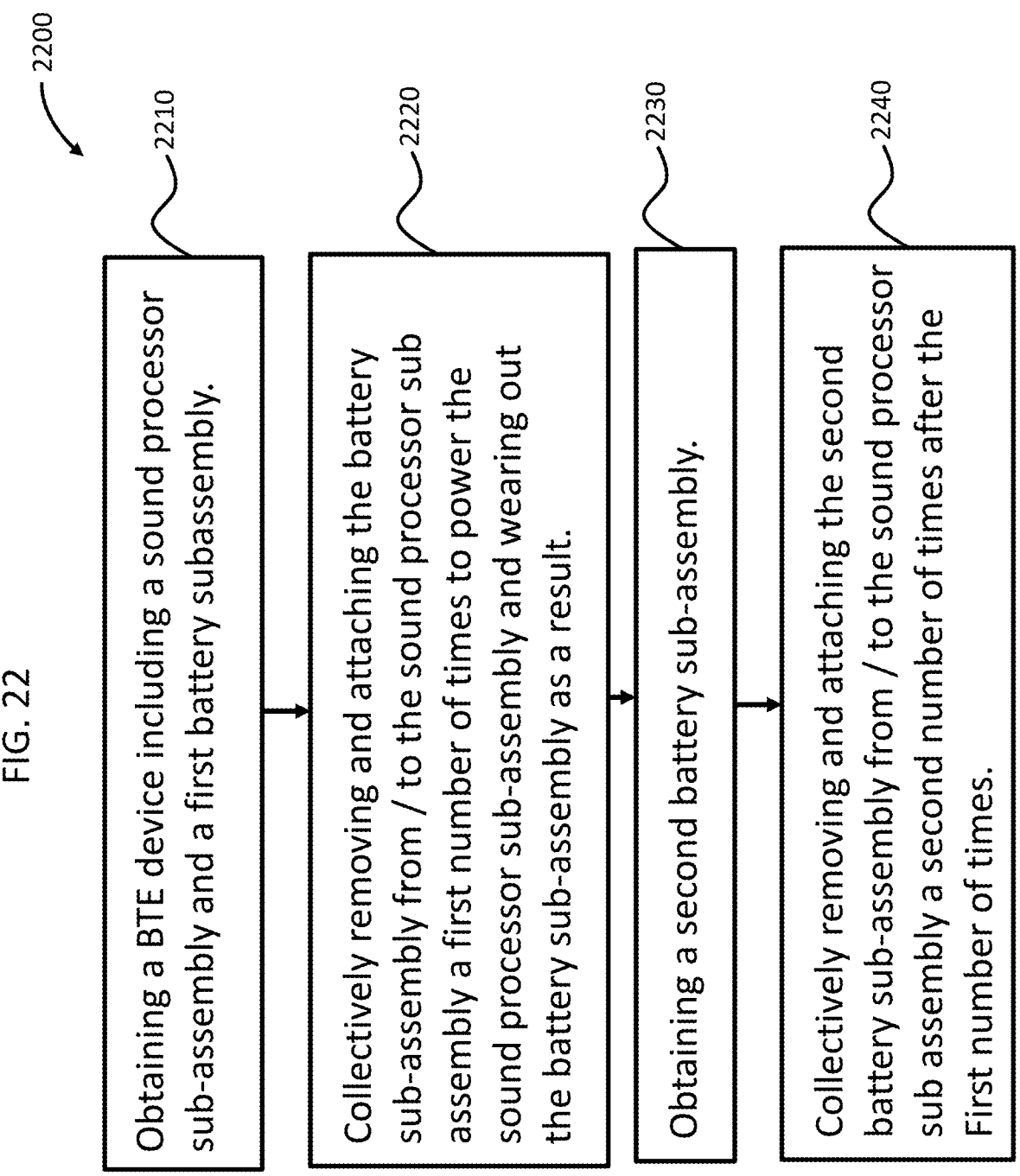
FIGS. 22 and 23 represent exemplary flowcharts for some exemplary embodiments of exemplary methods according to exemplary embodiments.

FIG. 22 presents a flowchart for an exemplary method, method 2200 according to an exemplary embodiment. Method 2200 includes method action 2210, which includes obtaining a BTE device, such as any of the BTE devices detailed herein and variations thereof. Method 2200 further includes method action 2220, which includes collectively removing and attaching the battery sub-assembly from/to the sound processor sub-assembly to power the sound processor sub-assembly a first number of times and wearing out the battery sub-assembly as a result. By way of example, this includes removing the battery and attaching the battery (collectively equaling one time of the first number of times) each day for 730 days or so, thus equaling 730 times, where about 2 years of such use is the life expectancy. The wearing out of the battery sub-assembly can be a result of the wearing of the connector portion of the battery sub-assembly and/or wearing out the battery cells of the battery assembly. Method 2200 further includes method action 2230, which includes obtaining a second battery sub-assembly, and method action 2240, which includes collectively removing and attaching the second battery sub-assembly from/to the sound processor sub assembly a second number of times after the first number of times. In an exemplary embodiment, the second battery sub-assembly is a replacement for the now worn-out first battery sub-assembly. In this method, the second number of times is at least half the first number of times. In an alternate embodiment of this method, the second number of times is at least 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 times the first number of times.

Figure 23:
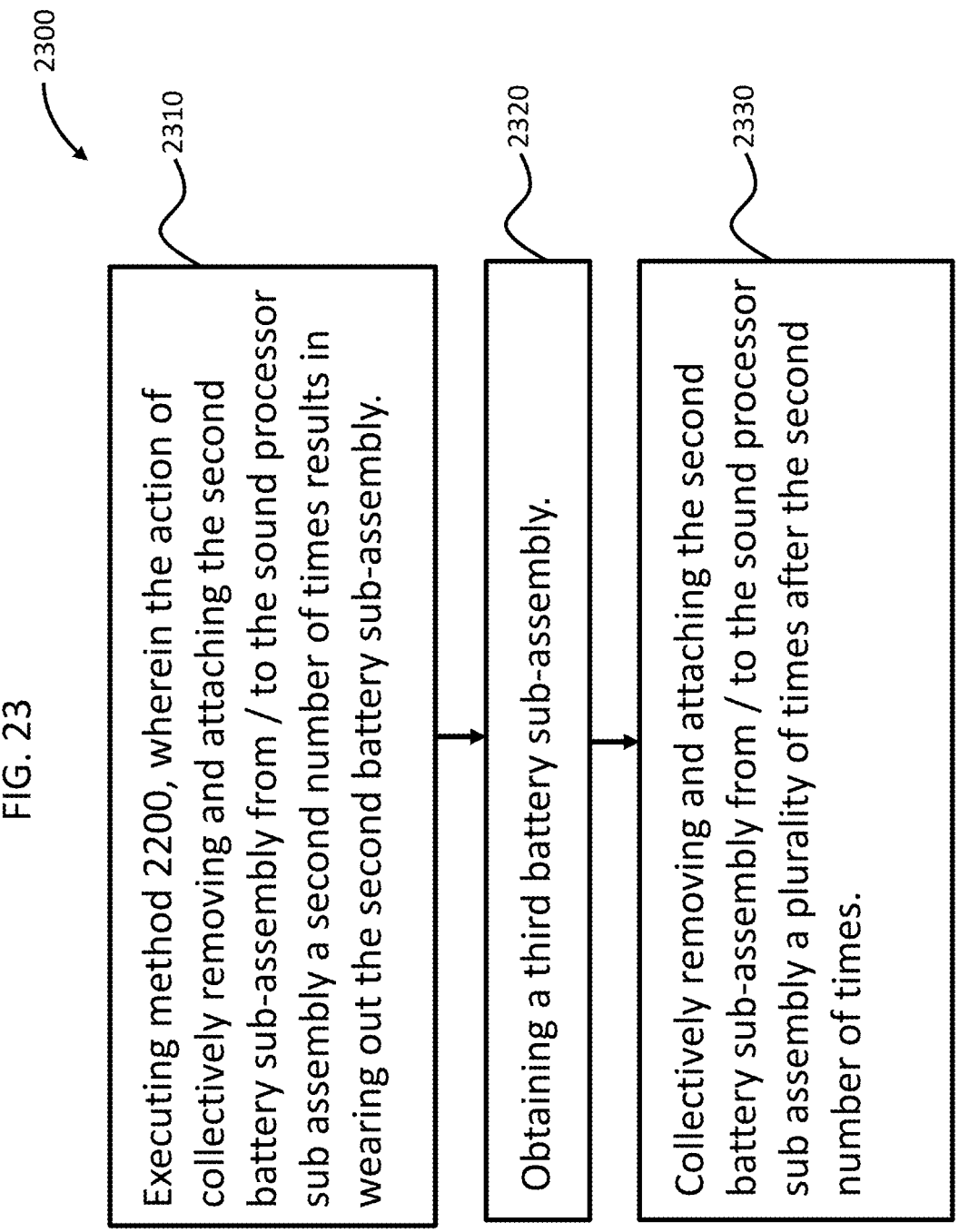

FIG. 23 presents another exemplary flowchart for an exemplary method, method 2300, according to an exemplary embodiment. Method 2300 includes method action 2310, which includes executing method 2200, wherein the action of collectively removing and attaching the second battery sub-assembly from/to the sound processor sub assembly a second number of times results in wearing out the second battery sub-assembly, due to, for example, wear of the attachment components and/or wear of the battery cells, etc. Method 2300 further includes method action 2320, which includes obtaining a third battery sub-assembly. In an exemplary embodiment, this obtained third battery sub-assembly is a replacement for the now worn-out second battery sub-assembly. (It is briefly noted that the obtained new batteries can be obtained before the first number of times and the second number of times is executed, respectively. That is, in some exemplary embodiments, the new battery can be a battery that the recipient has previously obtained, but simply has not used. Conversely, this new battery can be a new battery that the recipient has previously used, but now it is a replacement for the now worn-out first or second battery. In this regard, it is noted that the usages of the first, second, and third batteries, etc., can overlap. It is the number of times according to the method claims that do not overlap. If the old battery is again used, the number of times according to the method claims resets to zero.)

Method 2300 further includes method action 2330, which includes collectively removing and attaching the second battery sub-assembly from/to the sound processor sub assembly a plurality of times after the second number of times. In an exemplary embodiment the plurality of times corresponds to at least 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 times the first number of times.

The concept associated with the methods detailed above is that the sound processor sub-assembly can be utilized for a period of time longer than the life of the batteries that are used to power the sound processor sub-assembly, and this is at least partially due to the fact that the connector portions of the sound processor sub-assembly are configured to last longer than the connector portions of the battery sub-assembly, or, more accurately, the connector portions of the battery sub-assembly specifically designed to fail before the connector portions of the sound processor sub-assembly. Indeed, in an exemplary embodiment, the idea is that the connector portions of the battery subassemblies impart little to no wear onto the connector portions of the sound processor sub-assembly.

As an aside, it is noted that in at least some exemplary scenarios of use, the recipient will have two or more batteries that will be used with the sound processor sub-assembly, typically in a serial manner with respect to depleting the charges of the respective batteries. As noted above, two or more batteries could be changed out from the same sound processor sub-assembly in a given day: the above noted battery A and battery B exemplary scenario. Accordingly, with respect to the aforementioned methods, the first number of times is only directed to battery A or Battery B. That is, the first number of times is not cumulative between the two batteries. Thus, in at least some exemplary embodiments, method 2200 and/or method 2300 is being practiced twice in a simultaneous manner: one for battery A and one for battery B. It is to be understood that there is no requirement for the batteries to be switched out in a serial manner. By way of example only and not by way of limitation, battery A could be used and then the charge depleted, and then removed and recharged, and then again attached to the sound processor sub-assembly without utilizing battery B in between. A scenario of use could be A, A, A, B, B, A, B, A, B, A, B, B, A, B, A, A, A, B, A. This would amount to 11 first times for battery A and 8 first times for battery B. In an exemplary scenario of use, battery A could be used 1000 times by the time that battery B is used 500 times, and if the $1000^{th}$ time wears out battery A, and then battery C is introduced after battery A is stopped being utilized, and battery B and battery C by the batteries that are being switched out, the method applicable to battery A and battery C would be on the second number of times, while the method applicable to battery B and the as yet unused battery D would be on the first number of times.

It is briefly noted that with respect to the above noted seals (e.g., the seal 433, the seal between the ribs 454 and the plastic component 434, etc.), the seals can be configured to have a life expectancy longer than that of the battery subassembly and/or have a life expectancy as long as that of the sound processor subassembly. With respect to the former, they can have utilitarian value with respect to placing the seal(s) on the battery subassembly so that when a new battery subassembly is obtained, new seals are obtained. In an exemplary embodiment, the seals utilized herein are configured to withstand at least 1000, 1200, 1400, 1600, 1800, 2000, 2200, 2200, 2600, 2800, 3000, 3200, 3400, 3600, 3800, or 4000 or more complete removal and attachment cycles of the battery (e.g., if battery A and battery B are both attached and detached from the sound processor sub-assembly during a given day, the seal would withstand 2000 days of use if the seal was on the sound processor subassembly, and 4000 days of use if the seals were respectively on the battery subassemblies (if the battery subassemblies would last so long).

Figure 24:
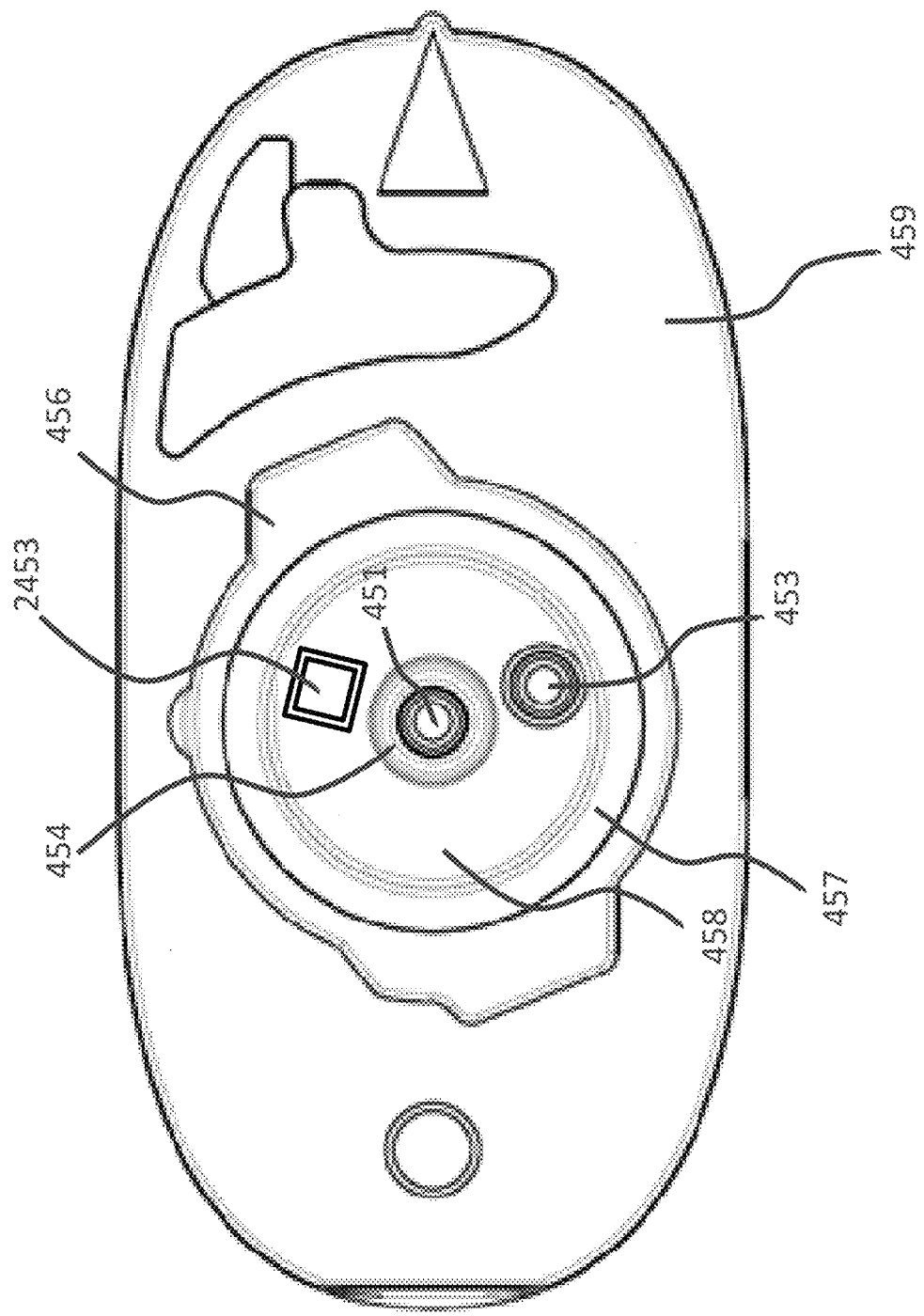
FIGS. 24-33 represent alternate embodiments of the coupling assembly of the battery sub-assembly.

FIG. 24 presents a top view of an alternate embodiment of a connector assembly of the battery subassembly. As can be seen, contact pin 2453 has a square shape/a square cross-section, as opposed to a round shaped/round cross-section as is the case with contact 453. While only one contact is depicted as being square, in some embodiments, both contacts can be square. Also, while the embodiment of FIG. 24 depicts a square cross-sectioned contact pin 2453, in an alternate embodiment, the cross-section can be rectangular. Note further, that oval-shaped cross-sections and/or triangular-shaped cross-sections can be utilized. It is also noted that the various shapes of the contacts of the connector assembly of the battery subassembly can also be utilized with the contacts of the connector assembly of the sound processor subassembly (the contacts can be different as well—e.g., square cross-sectioned contacts be utilized on the sound processor subassembly and triangular cross-sectioned contacts can be utilized on the battery subassembly. Any configuration of pin can be utilized if such can yield utilitarian value.

Figure 25:
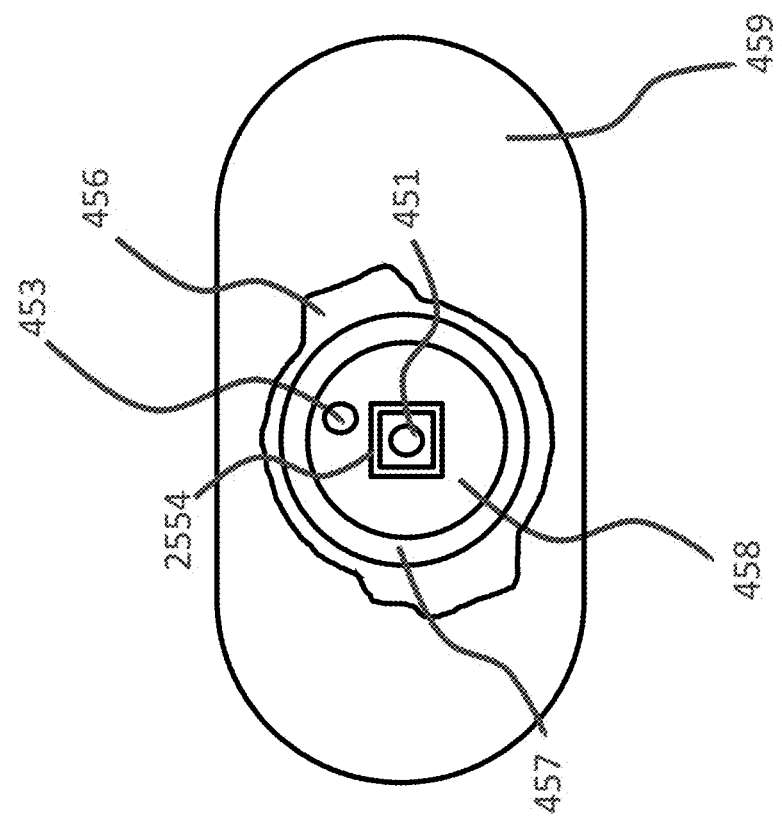
Figure 26:
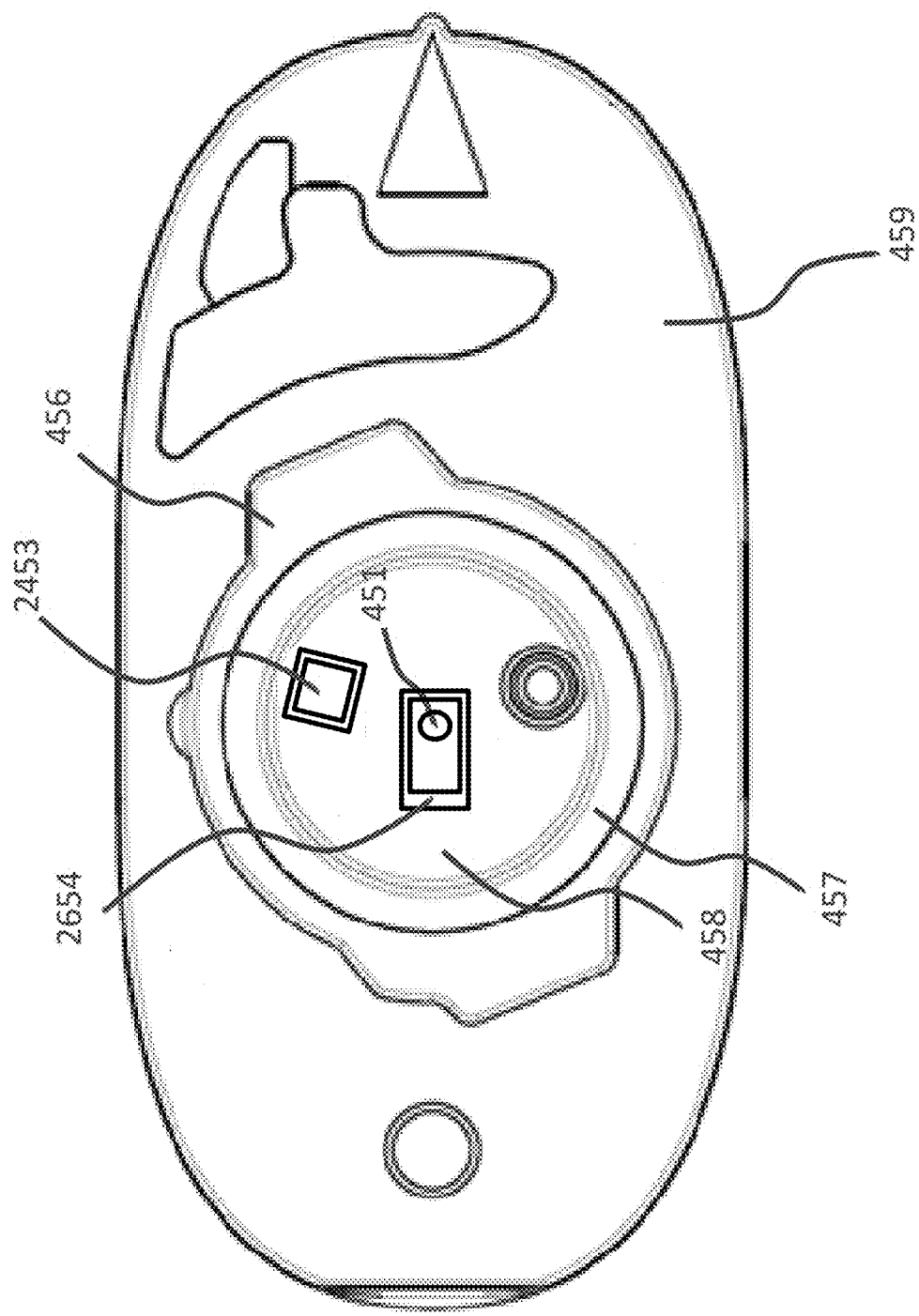
Figure 27:
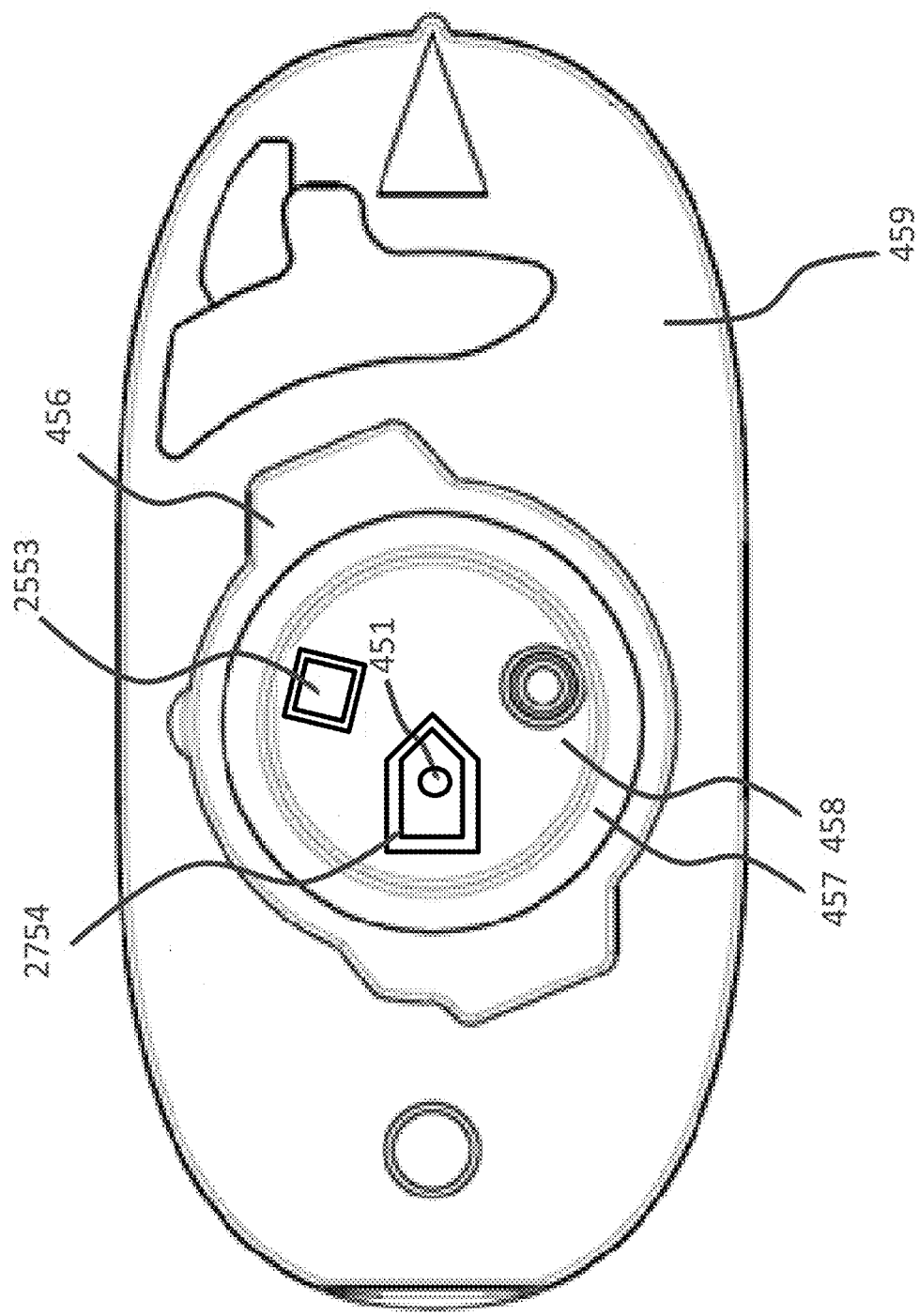

FIG. 25 presents a top view of an alternate embodiment of a connector assembly of the battery assembly. Here, there is only one positive contact 453. Also, the rib/barrier about contact 451 extends about contact 451 in a squareshape, as opposed to a circular shape. FIG. 26 depicts an alternate embodiment where the rib 2654 that extends about the contact 451 is rectangular when viewed from the top, and also the contact 451 is not centered within the area within the rib. FIG. 27 depicts the barrier 2754 extending about the contact 451 in a five sided shape, which in some embodiments can be a perfect pentagon. Also, as can be seen, the contact 451 is not centered within the basin 458. Instead, the contact 451 is off-center. Any arrangement that can enable the teachings detailed herein to have utilitarian value can be utilized in at least some exemplary embodiments.

Figure 28:
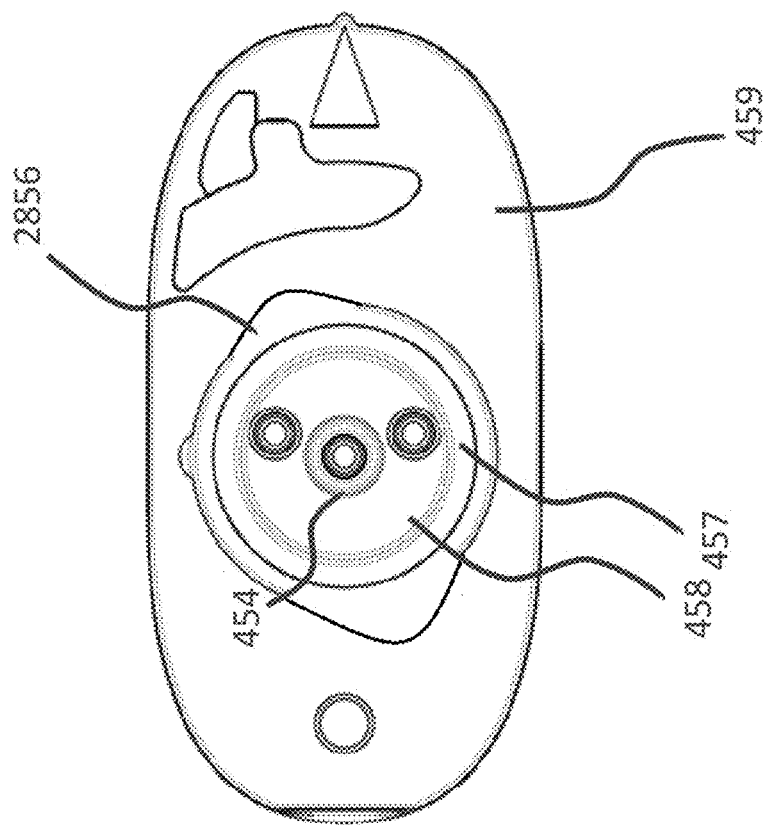
Figure 29:
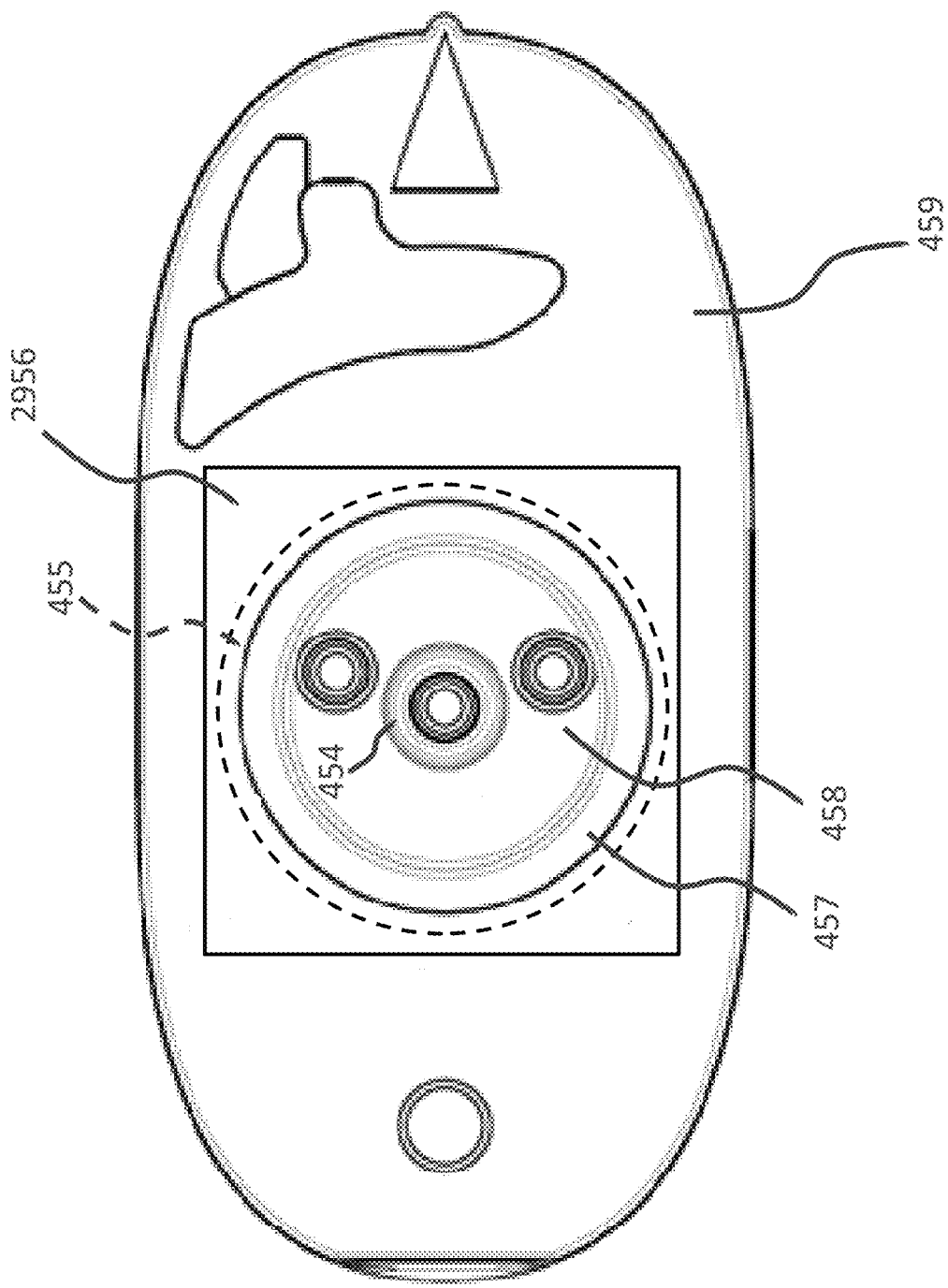
Figure 30:
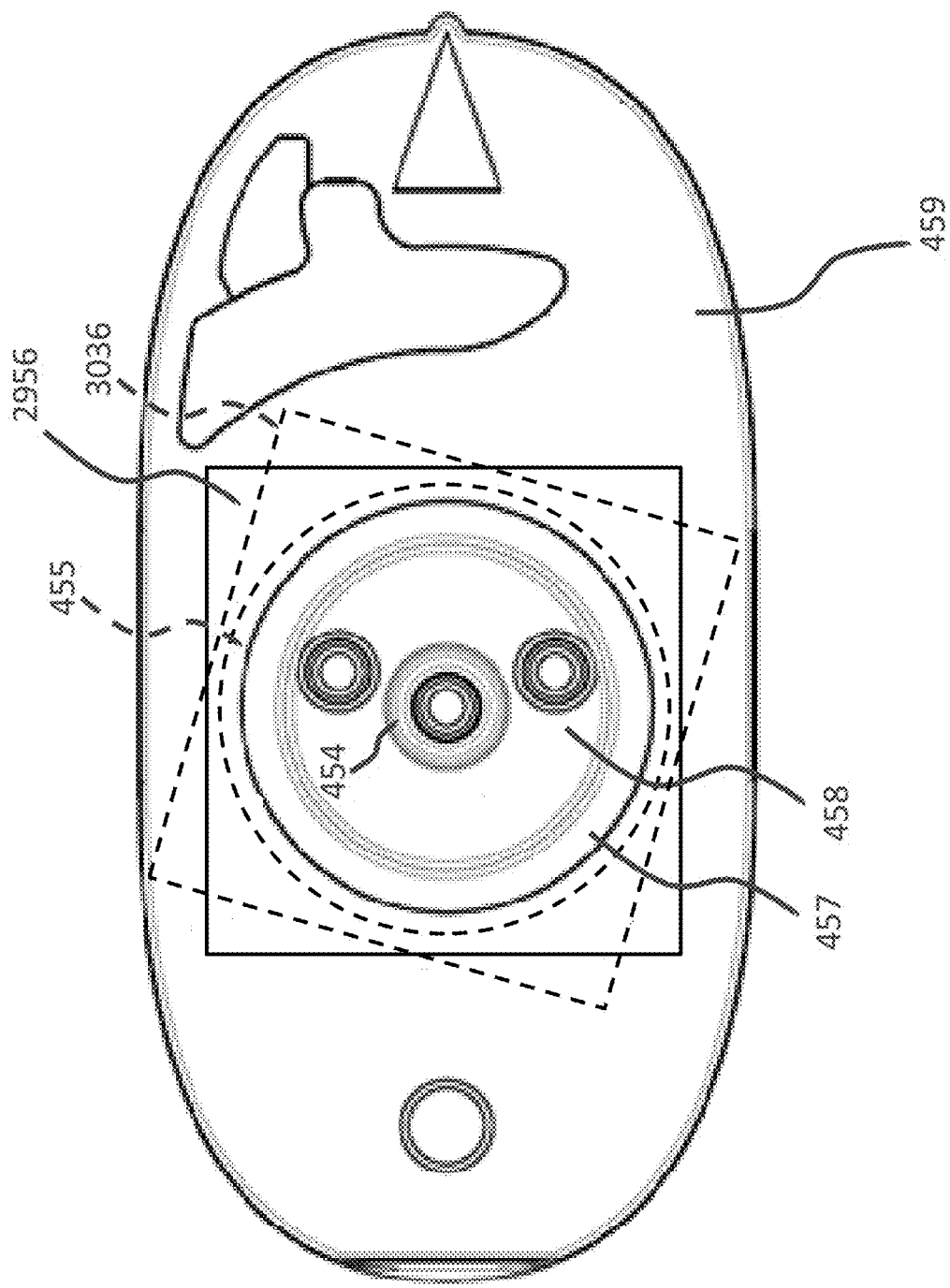

FIG. 28 depicts an alternate embodiment of the connector assembly of the battery subassembly where the wings of the male portion of the bayonet connector are curved as can be seen. It is to be understood that the corresponding female components of the bayonet connector of the sound processor subassembly are similarly matched so as to receive wings 2856. FIG. 29 depicts another alternative embodiment where the wing(s) are established by a square plate 2956 located atop the bayonet coupling 455. In an exemplary embodiment, the female portion of the bayonet coupling of the sound processor subassembly includes a female opening having a square shape that receives the plate 2956. Upon rotation of the battery subassembly relative to the sound processor subassembly, the tips of the square female section slide under the tips of the plate 2956, as depicted by way of example in FIG. 30, where reference number 3036 corresponds to a functional equivalent of the wings 436 of the female component described above, where the position of 3036 is in the fully attached position (the battery subassembly and the sound processor subassembly are aligned with each other/fully seated with respect to each other). As can be seen, because the respective squares of the male portion and the female portion of the bayonet connector are not aligned when the subcomponents are fully seated with respect to each other, the portions overlap and thus tell the two subcomponents to each other.

Figure 31:
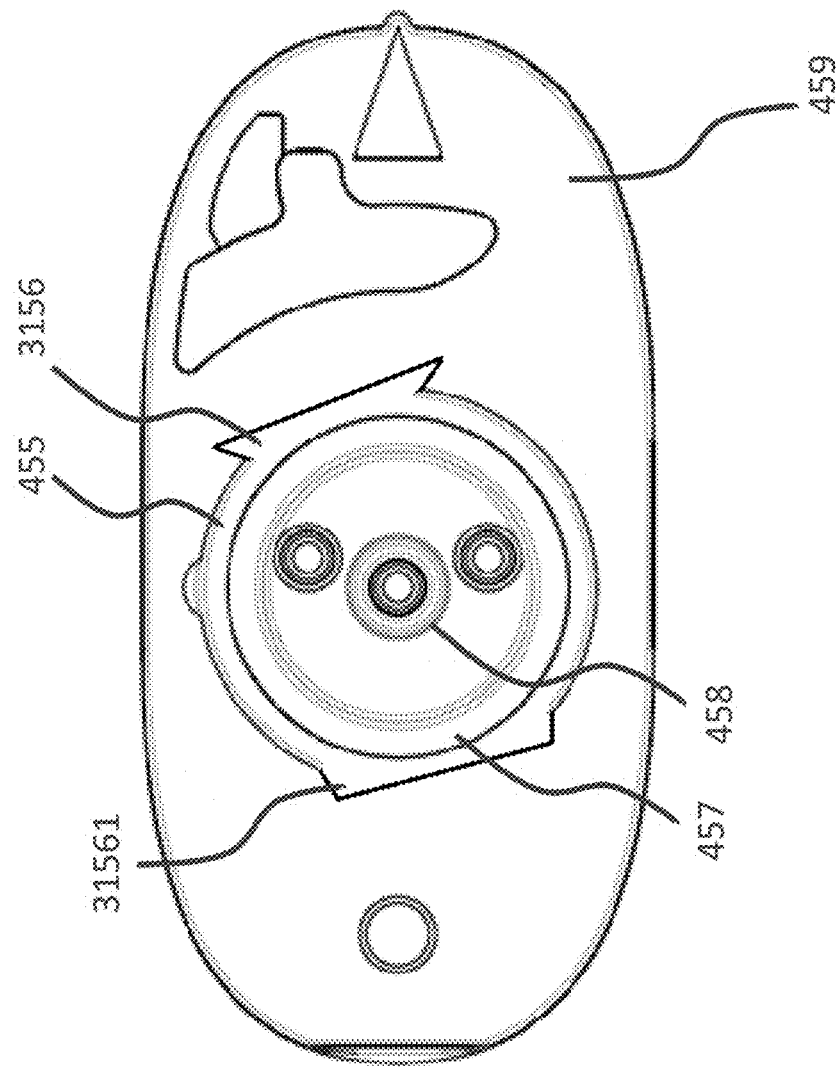
Figure 32:
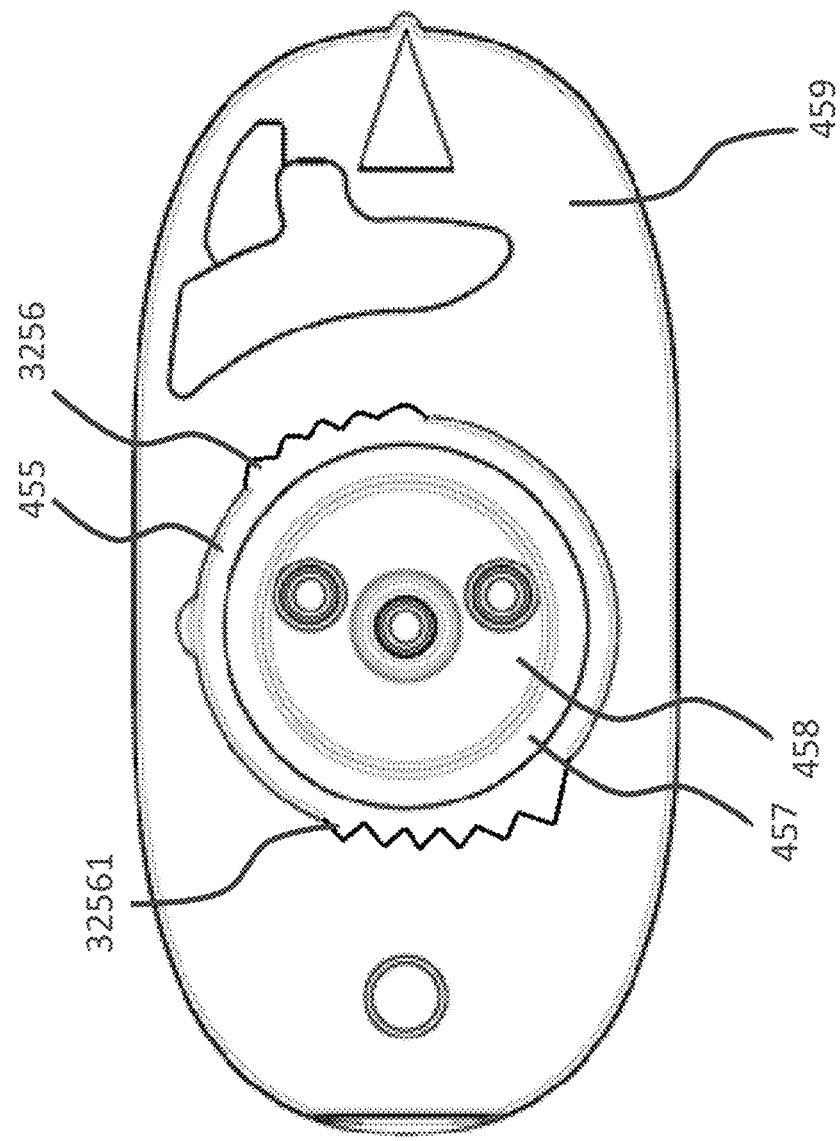
Figure 33:
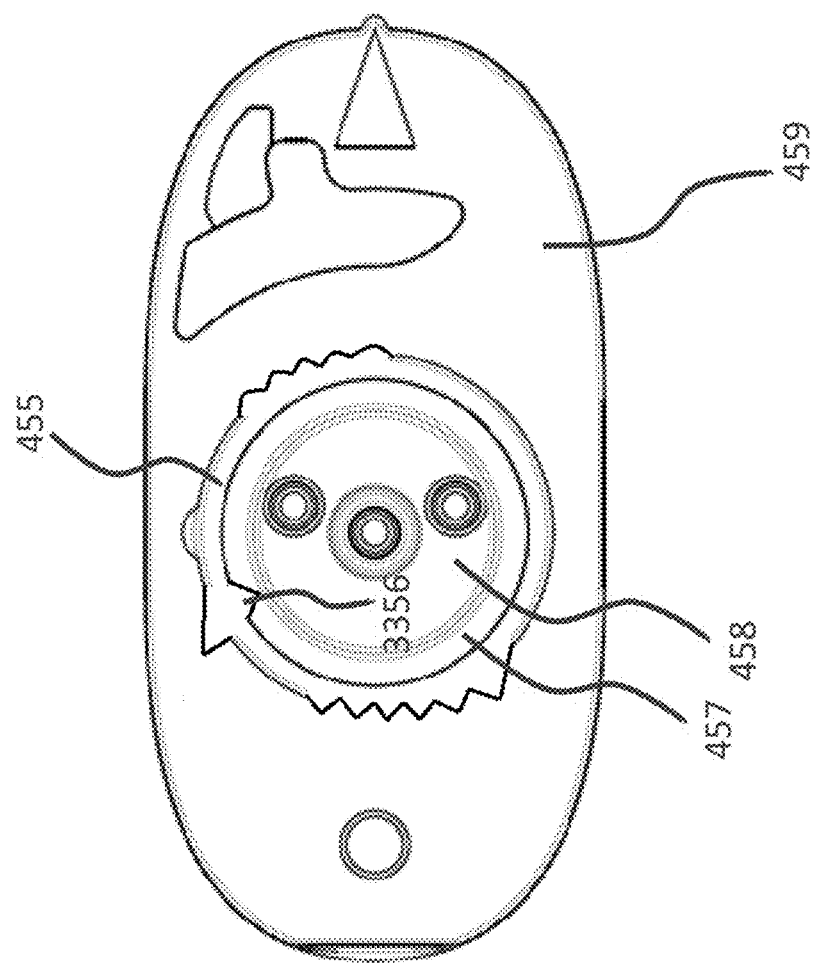

FIG. 31 depicts another alternative embodiment of the connector assembly for the battery subassembly. Here, wings 3156 and 31561 of a different configuration than the wings described above can be seen. It is noted that respective female portions of the sound processor subassembly can be similarly shaped, albeit in a female configuration, to receive these components and permit the male component to be twisted therein so as to fully secure the battery subassembly to the sound processor subassembly. FIG. 32 presents yet further exemplary embodiments of wings 3256 and 32561, as can be seen. FIG. 33 includes components corresponding to the embodiment of FIG. 32, but also includes a wing 3356, which extends inboard of the male portion of the bayonet coupling instead of outboard as is the case with respect to the wings detailed above. It is noted that in at least some exemplary embodiments, corresponding female portions of the sound processor subassembly are sized and dimensioned to receive these components and enable the twisting of the two subcomponents relative to one another so as to fully seat the connector assemblies.

Figure 34:
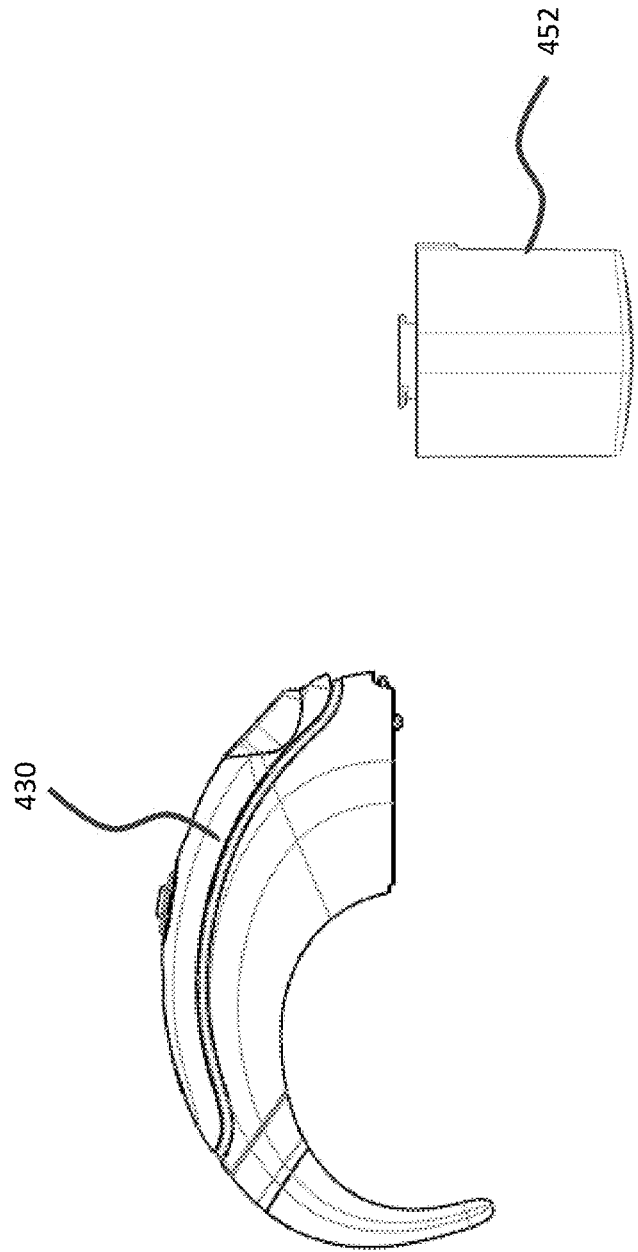
FIGS. 34-36 schematically depict an alternate configuration where the battery sub-assembly is laterally moved to connect to the sound processor sub-assembly.
Figure 35:
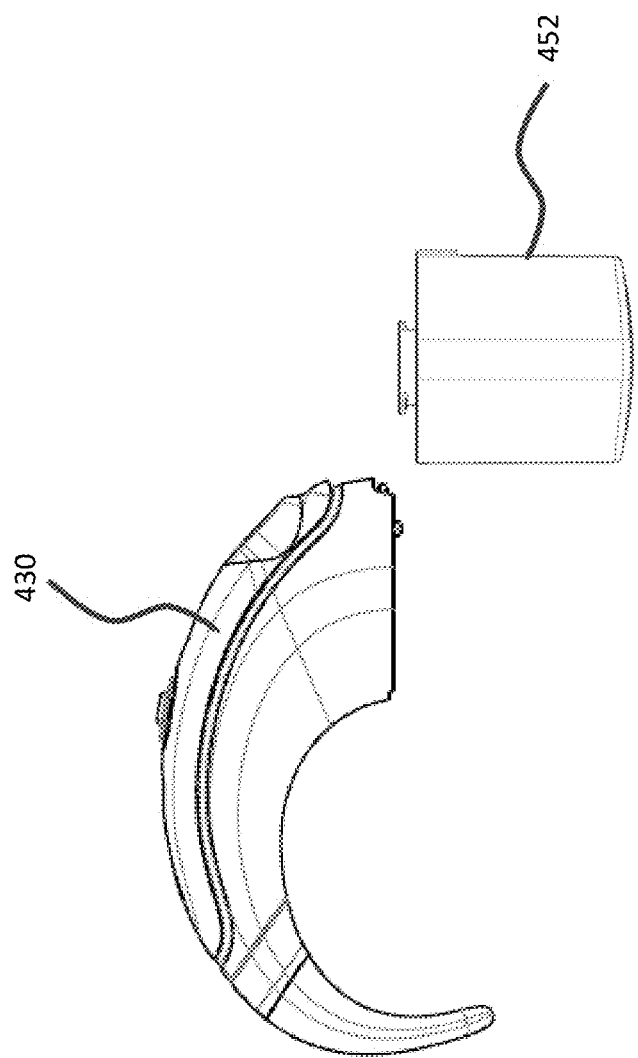
Figure 36:
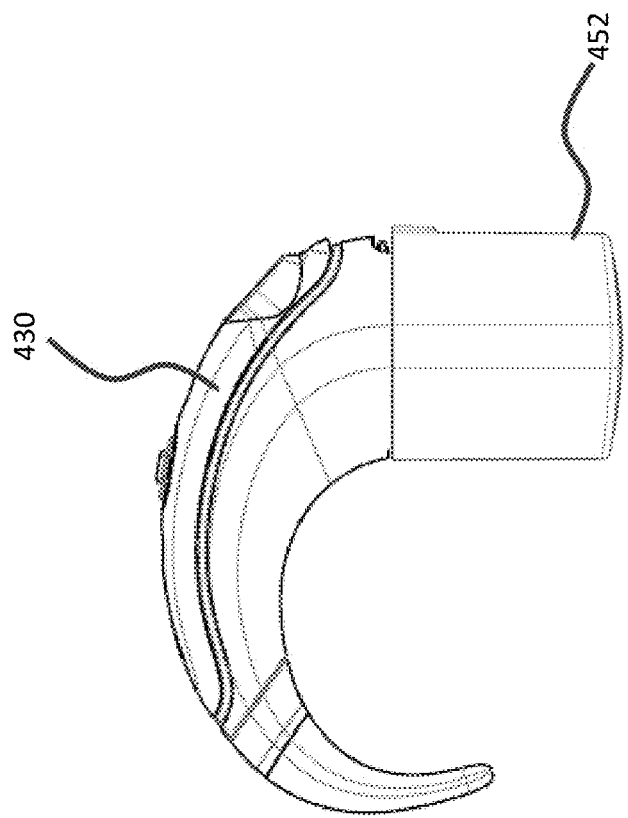

It is also noted that while the embodiments detailed above have focused on the male portion of the bayonet coupling being on the battery subassembly and the female portion of the bayonet coupling being on the sound processor subassembly, in some alternate embodiments, the reverse is the case. That is, the female portion of the banner coupling can be located on the battery subassembly, and the male portion of the bayonet coupling can be located one the sound processor subassembly. Any arrangement of any component of the connector assemblies of the battery subassembly and the sound processor subassembly that can have utilitarian value can be utilized in at least some exemplary embodiments. Literally any shape or configuration or dimensioning that can enable the removal and replacement of the battery subassembly from the sound processor subassembly can be utilized. Indeed, while the embodiments above have focused on an arrangement where a bayonet coupling is utilized so that the battery subassembly 452 can be moved in the vertical direction/in the longitudinal direction of the battery subassembly up to the sound processor subassembly 430 and then turned to couple the two subcomponents together in the traditional manner of a bayonet coupling, in an alternative embodiment, such as is schematically illustrated in FIGS. 34, 35 and 36, the battery subassembly 452 is moved in the lateral direction so as to connect to the sound processor subassembly 430, and moved in the opposite direction so as to disconnect from the sound processor subassembly 430. In such an embodiment, in at least some exemplary embodiments, instead of a bayonet coupling, a different type of coupling is utilized, such as a C shape female slotted connector and a male shape T extruded connector, where the head of the T fits into the concave portion of the C in a sliding manner (where the C and the T extend inward and outward of this page). Consistent with the above embodiments, the male portion can be on the battery assembly and the female portion can be on the sound processor subassembly or vice versa. Another type of coupling, such as a snap coupling, can be utilized in at least some alternative embodiments. Any arrangement whatsoever that can enable the battery subassembly to be removably coupled to the sound processor subassembly can be utilized at least some exemplary embodiments.

In an exemplary embodiment, there is an external device of a prosthesis, such as a BTE device or a button sound processor device, comprising an electronics component; and a power component, removably attached to the electronics component, wherein the external device is configured with electrical current protection at a plug-socket arrangement connecting the power component to the electronics component. In an exemplary embodiment, there is an external device of a prosthesis, such as a BTE device or a button sound processor device, described above or below, wherein the external device is configured to frustrate electrostatic discharge to active electrical contact(s) of the electronics component from the power component and encourage electrostatic discharge to passive electrical contact(s) of the electronics component from the power component to the extent that electrostatic discharge will occur when the power component is connected to the electronics component. In an exemplary embodiment, there is an external device of a prosthesis, such as a BTE device or a button sound processor device, described above or below, wherein the electronics component includes a socket having an electrically conductive body; the power component includes a plug having an electrically conductive body, the plug having a basin in which electrical contacts are present; and an electrostatic discharge limiting component is located between at least one of the electrically conductive body of the power component or the electrically conductive body of the socket and the electrical contacts when the power component is at least initially connected to the electronics component. In an exemplary embodiment, there is an external device of a prosthesis, such as a BTE device or a button sound processor device, described above or below, wherein the electronics component includes a socket having an electrically conductive body; the power component includes a plug having an electrically conductive body, the plug having a basin in which electrical contacts are present; an electrostatic discharge shield is located between the electrically conductive body of the power component and the electrical contacts; and the electrically conductive bodies are respectively configured to provide mechanical releasable coupling of the power component to the electronics component.

In an exemplary embodiment, there is an external device of a prosthesis, such as a BTE device or a button sound processor device, described above or below, wherein the power component and the electronics component respectively have apparatuses of a bayonet coupling configured to removably attach the components together; the power component includes a positive terminal and a negative terminal of a battery; the electronics component includes a first contact and a second contact electrically isolated from the first contact; the first contact is configured to be in electrical contact with the positive terminal and the second contact is configured to be in electrical contact with the negative terminal when the power component is fully attached to the electronics component; and the bayonet coupling is configured such that the negative terminal comes into electrical contact with the second contact before the positive terminal comes into contact with the first contact when the power component is initially attached to the electronics component.

In an exemplary embodiment, there is an external component of a prosthesis, such as a behind-the-ear (BTE) device, or a button sound processor, including a sound processor sub-assembly and a battery sub-assembly, removably attached to the sound processor sub-assembly, wherein the BTE device or button sound processor is configured such that the apparatus of the battery sub-assembly that enables the removable attachment to the sound processor sub-assembly will wear out before the apparatus of the sound processor sub-assembly that enables removable attachment to the battery sub-assembly due to repeated removal and attachment of the battery sub-assembly from/to the sound processor sub-assembly. In an exememplary embodiment, there is the BTE device or button sound processor as just described, wherein at least some surfaces of the apparatus of the sound processor sub-assembly that enable removable attachment to the battery sub-assembly are harder than at least some interfacing surfaces of the apparatus of the battery sub-assembly that enable removable attachment to the sound processor sub-assembly.

In an exemplary embodiment, there is an external device of a prosthesis, such as a behind-the-ear (BTE) device or a button sound processor, comprising an electronics component; and a power component, removably attached to the electronics component, wherein the device is configured with an environmental barrier at the general interface between the electronics component and the power component. In an exemplary embodiment, there is an external device of a prosthesis, such as a behind-the-ear (BTE) device or a button sound processor, as described above and/or below, wherein the power component includes a planar body from which a plug rises, the plug being formed by a first circular rib, the first circular rib encompassing a first electrical contact and a second electrical being of a different polarity than the first electrical contact; and a second circular rib encompasses the first electrical contact and forms, at least with the aid of gravity, a liquid barrier between the first electrical contact and the second electrical contact. In an exemplary embodiment, there is an external device of a prosthesis, such as a behind-the-ear (BTE) device or a button sound processor, as described above and/or below, wherein the power component includes a first electrical contact and a second electrical contact electrically isolated from the first electrical contact and being of a different polarity than the first electrical contact; and the power component includes a liquid barrier between the first electrical contact and the second electrical contact. In an exemplary embodiment, there is an external device of a prosthesis, such as a behind-the-ear (BTE) device or a button sound processor, as described above and/or below, wherein the liquid barrier is also a gas barrier.

In an exemplary embodiment, there is the BTE device or button sound processor as just described, wherein at least some surfaces of the apparatus of the sound processor sub-assembly that enable removable attachment to the battery sub-assembly that interface with surfaces of the apparatus of the battery sub-assembly that enable removable attachment to the sound processor sub-assembly are nickel containing surfaces. In an exememplary embodiment, there is the BTE device or button sound processor as just described, wherein at least some surfaces of the apparatus of the sound processor sub-assembly that enable removable attachment to the battery sub-assembly that interface with surfaces of the apparatus of the battery sub-assembly that enable removable attachment to the sound processor sub-assembly comprise nickel PTFE coated titanium. In an exememplary embodiment, there is the BTE device or button sound processor as just described, wherein the apparatus that enables removable attachment corresponds to a bayonet connector. In an exememplary embodiment, there is the BTE device or button sound processor as just described, wherein the apparatus of the sound processor sub-assembly that enables removable attachment to the battery sub-assembly that interfaces with surfaces of the apparatus of the battery sub-assembly that enables removable attachment to the sound processor sub-assembly are heat treated to a first hardness; and the apparatus of the battery sub-assembly that enables removable attachment to/from the sound processor sub-assembly that interface with surfaces of the apparatus of the sound processor sub-assembly that enables removable attachment to/from the battery sub-assembly are one of a non-heat treated apparatus having a second hardness less than the first hardness or a heat-treated apparatus heat treated such that the apparatus has a third hardness less than the first hardness. In an exememplary embodiment, there is the BTE device or button sound processor as just described, wherein at least a portion of the apparatus of the battery sub-assembly that enables removable attachment to the sound processor sub-assembly is imbedded in an injection molded plastic body of the battery sub-assembly.

In an exemplary embodiment, there is a method, comprising obtaining the BTE device or button sound processor device noted above, collectively removing and attaching the battery sub-assembly from/to the sound processor sub-assembly a first number of times to power the sound processor sub-assembly and wearing out the battery sub-assembly as a result, obtaining a second battery sub-assembly, and collectively removing and attaching the second battery sub-assembly from/to the sound processor sub assembly a second number of times after the first number of times; wherein the second number of times is at least half the first number of times. In some embodiments, the method just noted is such that the action of collectively removing and attaching the second battery sub-assembly from/to the sound processor sub assembly a second number of times results in wearing out the second battery sub-assembly; method further comprises obtaining a third battery sub-assembly; and collectively removing and attaching the second battery sub-assembly from/to the sound processor sub assembly a plurality of times after the second number of times.

It is noted that any embodiment or feature disclosed herein associated with one embodiment can be combined with any other embodiment or any other feature disclosed herein associated with another embodiment unless otherwise specified or unless the art does not enable such. It is further noted that any disclosure herein of a device and/or system further corresponds to a disclosure of a method action of utilizing that device and/or system. Corollary to this is that any disclosure herein of a method action corresponds to a disclosure method action of a device and/or system for executing that method action. It is also noted that any method action herein detailed with respect to fabricating or otherwise making a device and/or system corresponds to a resulting device and/or system that results from that fabrication action. It is also noted that any device and/or system detailed herein corresponds to a disclosure of a method of making that device and/or system.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A behind-the-ear (BTE) device, comprising:
an electronics component; and
a power component, removably attached to the electronics component, wherein
the BTE device is configured with an environmental barrier at a general interface between the electronics component and the power component, wherein at least one of:
(i) the BTE device includes a plug and a moisture resistant seal, the electronics component and the power component are configured to rotate relative to one another to removably connect the power component to the electronics component, and the plug slides along a surface of the moisture-resistant seal during the rotation; or
(ii) the power component includes a planar body from which a crater-like component rises, the crater-like component including a crater wall and a central peak in which a first electrical contact is located, the crater wall surrounding the central peak, and a second contact is located between the crater wall and the central peak, the second contact being of an opposite polarity than the first contact.

2. The BTE device of claim 1, wherein:
the environmental barrier is a moisture barrier.

3. The BTE device of claim 2, wherein:
the environmental barrier is a means for environmental blocking.

4. The BTE device of claim 2, wherein:
an entire circumference of the environmental barrier is visible when the electronics component is detached from the power component.

5. The BTE device of claim 2, wherein:
the environmental barrier is in contact with the electronics component when the power component is removably attached to the electronics component.

6. The BTE device of claim 2, wherein:
the environmental barrier is configured to prevent moisture from reaching contact locations of respective contacts of the electronics component and the power component when the power component is removably attached to the electronics component.

7. The BTE device of claim 1, wherein:
the electronics component and the power component are configured to rotate relative to one another to removably connect the power component to the electronics component; and
the plug slides along the surface of the moisture-resistant seal during the rotation.

8. The BTE device of claim 1, wherein:
the power component includes the planar body from which the crater-like component rises, the crater-like component includes the crater wall and the central peak in which the first electrical contact is located, the crater wall surrounding the central peak;
the second contact is located between the crater wall and the central peak, the second contact being of the opposite polarity than the first contact.

9. The BTE device of claim 1, wherein:
the power component includes a positive terminal and a negative terminal of a battery;
the electronics component includes a first contact and a second contact electrically isolated from the first contact;
the first contact is configured to be in electrical contact with the positive terminal and the second contact is configured to be in electrical contact with the negative terminal when the power component is fully attached to the electronics component; and
the BTE device is configured such that the negative terminal comes into electrical contact with the second contact before the positive terminal comes into contact with the first contact when the power component is initially attached to the electronics component.

10. The BTE device of claim 9, wherein:
at least one of the negative terminal or the second contact is biased in a longitudinal direction of the respective BTE device component so as to provide give in the longitudinal direction when the components are attached to one another to enable the first contact to come into electrical contact with the positive terminal.

11. The BTE device of claim 1, wherein:
the power component is a battery sub-assembly with all electrical contacts of the battery on one side thereof and the electronics component is an electronics sub-assembly of the BTE device.

12. A behind-the-ear (BTE) device, comprising:
an electronics component; and
a power component, removably attached to the electronics component, wherein
the BTE device is configured with an environmental barrier at a general interface between the electronics component and the power component, wherein
the power component includes a positive terminal and a negative terminal of a battery,
the electronics component includes a first contact and a second contact electrically isolated from the first contact,
the first contact is configured to be in electrical contact with the positive terminal and the second contact is configured to be in electrical contact with the negative terminal when the power component is fully attached to the electronics component, and
at least one of:
at least one of the negative terminal or the second contact is biased in a lateral direction of the respective BTE device component so as to provide give in the lateral direction when the components are attached to one another to enable the first contact to come into electrical contact with the positive terminal; or at least one of the negative terminal or the second contact is biased in a longitudinal direction of the respective BTE device component so as to provide give in the longitudinal direction when the components are attached to one another to enable the first contact to come into electrical contact with the positive terminal.

13. The BTE device of claim 12, wherein:
the electronics component includes a socket;
the power component includes a plug having a basin in which electrical contacts are present; and
the BTE device is configured to frustrate water intrusion into the basin when the power component is fully removably attached to the electronics component.

14. The BTE device of claim 12, wherein:
the electronics component includes a socket;
the power component includes a plug having a basin in which electrical contacts are present; and
a moisture-resistant seal is located between a surface of the socket and a surface of the plug, the moisture-resistant seal being configured to provide a seal about the basin when the power component is attached to the electronics component.

15. The BTE device of claim 12, wherein:
the electronics component includes a plurality of electrical terminals; and
all electrical terminals of the electronics component are only power transfer terminals for powering the electronics component.

16. The BTE device of claim 15, wherein:
the power component is a means for supplying power to the electronics component.

17. The BTE device of claim 12, wherein:
the electronics component and the power component are configured to rotate relative to one another to removably connect the power component to the electronics component to lock the power component to the electronics component.

18. The BTE device of claim 12, wherein:
at least one of the negative terminal or the second contact is biased in a lateral direction of the respective BTE device component so as to provide give in the lateral direction when the components are attached to one another to enable the first contact to come into electrical contact with the positive terminal.

19. A behind-the-ear (BTE) device, comprising:
an electronics component; and
a power component, removably attached to the electronics component, wherein the BTE device is configured with an environmental barrier at a general interface between the electronics component and the power component, wherein
the power component has a height that is about that of a height of the electronics component when measured in the same direction as the height of the electronics component, wherein the heights are measured in a vertical direction when the BTE device is worn behind the ear of a recipient, and
the BTE includes an earhook, a tip of the earhook being located below a plane extending normal to the same direction as the height of the electronics component, the plane being located at a location where the electronics component meets the BTE device when viewed from the outside, wherein the electronics component is located above the plane.

20. The BTE device of claim 19, wherein:
the power component has a height that is about that of a height of the electronics component when measured in the same direction as the height of the electronics component, wherein the heights are measured in a vertical direction when the BTE device is worn behind the ear of a recipient.

21. The BTE device of claim 19, wherein:
the battery sub-assembly is connected to the electronics sub assembly by a plug-socket arrangement; and
the environmental barrier is a distinct component from the plug and mounted on the plug.

22. The BTE device of claim 19, wherein:
the environmental barrier is a means for establishing an environmental barrier.

23. The BTE device of claim 19, wherein:
the environmental barrier is a ring that has a low friction coefficient relative to mating material of the BTE device at a sealing location of the environmental barrier.

24. The BTE device of claim 23, wherein:
the power component is a battery, and the BTE device is configured such that the battery establishes a base body of the BTE device that is contactable with skin of the recipient when the BTE device is worn behind the ear of a recipient.

25. The BTE device of claim 19, wherein:
the power component is only a power storage and transfer apparatus.

* * * * *